(12) United States Patent
Ren et al.

(10) Patent No.: US 10,571,448 B2
(45) Date of Patent: Feb. 25, 2020

(54) METHOD AND SYSTEM FOR COMPREHENSIVE EVALUATION OF ORGANIC COMPOUND AND HEAVY METAL POLLUTION IN WATER BASED ON FISH ELECTROCARDIO

(71) Applicants: SHANDONG NORMAL UNIVERSITY, Jinan, Shandong (CN); JINAN BIOSENSOR INSTRUMENT CO., LTD, Jinan, Shandong (CN); SOUTH CHINA INSTITUTE OF ENVIRONMENTAL SCIENCES. MEP, Guangzhou, Guangdong (CN)

(72) Inventors: Zongming Ren, Shandong (CN); Baichuan Ren, Shandong (CN); Linlin Qiao, Shandong (CN); Baixiang Ren, Shandong (CN); Yuedan Liu, Shandong (CN)

(73) Assignees: SHANDONG NORMAL UNIVERSITY, Jinan, Shandong (CN); JINAN BIOSENSOR INSTRUMENT CO., LTD, Jinan, Shandong (CN); SOUTH CHINA INSTITUTE OF ENVIRONMENTAL SCIENCES. MEP, Guangzhou (CN)

( * ) Notice: Subject to any disclaimer, the term of this patent is extended or adjusted under 35 U.S.C. 154(b) by 0 days.

(21) Appl. No.: 16/555,883

(22) Filed: Aug. 29, 2019

(65) Prior Publication Data

US 2020/0018738 A1 Jan. 16, 2020

Related U.S. Application Data

(63) Continuation of application No. PCT/CN2019/072599, filed on Jan. 22, 2019.

(30) Foreign Application Priority Data

Jul. 11, 2018 (CN) .......................... 2018 1 0759036
Oct. 15, 2018 (CN) .......................... 2018 1 1197170
(Continued)

(51) Int. Cl.
   *G01N 33/18* (2006.01)
   *A01K 61/10* (2017.01)
   (Continued)

(52) U.S. Cl.
   CPC .......... *G01N 33/186* (2013.01); *A01K 61/10* (2017.01); *A61B 5/0456* (2013.01);
   (Continued)

(58) Field of Classification Search
   CPC .............. G01N 33/186; G01N 33/1813; A61B 5/0468; A61B 5/0456; A61B 5/0472; A61B 2503/40; A01K 61/10
   (Continued)

(56) References Cited

U.S. PATENT DOCUMENTS

2012/0247395 A1* 10/2012 Koba ...................... A01K 63/00
                                                      119/207

FOREIGN PATENT DOCUMENTS

CN        107260163 A    * 10/2017
CN        107260163 A      10/2017
   (Continued)

OTHER PUBLICATIONS

Translation of JP-2009055799-A, Kojima et al (Year: 2009).*
Translation of CN-107260163-A, Jiang et al (Year: 2017).*

*Primary Examiner* — Nathaniel T Woodward
(74) *Attorney, Agent, or Firm* — Wayne & Ken, LLC; Tony Hom

(57) ABSTRACT

Disclosed are a method and a system for comprehensive evaluation of organic compound and heavy metal pollution
(Continued)

in water based on fish electro-cardio, and fish electro-cardio signals are acquired by a real-time and miniaturized fish electro-cardio acquisition system which includes a real-time and miniaturized fish electro-cardio acquisition device, then a change of the electro-cardio index in a QT interval is obtained for assessing the corresponding organic compound in water to be tested, and a change of the electro-cardio index in a QRS interval is obtained for assessing the corresponding heavy metal in water to be tested. Based on fish electro-cardio acquired continuously on-line in real-time while keeping fish swims in a normal state and the water quality parameters acquired by various water quality sensors, water quality is online analyzed and water sudden pollution is online monitored and assessed.

24 Claims, 10 Drawing Sheets

(30) Foreign Application Priority Data

Oct. 15, 2018 (CN) .......................... 2018 1 1197187
Dec. 21, 2018 (CN) .......................... 2018 1 1571919
Dec. 21, 2018 (CN) .......................... 2018 1 1572871

(51) Int. Cl.
*A61B 5/0468* (2006.01)
*A61B 5/0472* (2006.01)
*A61B 5/0456* (2006.01)

(52) U.S. Cl.
CPC .......... *A61B 5/0468* (2013.01); *A61B 5/0472* (2013.01); *G01N 33/1813* (2013.01); *A61B 2503/40* (2013.01)

(58) Field of Classification Search
USPC ........................................................ 73/61.42
See application file for complete search history.

(56) References Cited

FOREIGN PATENT DOCUMENTS

| CN | 109044343 | A |   | 12/2018 |
|----|-----------|---|---|---------|
| CN | 109222959 | A |   | 1/2019  |
| DE | 202013001370 | U1 |   | 5/2013 |
| JP | 2009055799 | A | * | 3/2009 |
| JP | 2009055799 | A |   | 3/2009 |

* cited by examiner

```
Inserting an electrode into a pericardial cavity of a fish to acquire original
electro-cardio signals and transmit the original electro-cardio signals to a
miniature electro-cardio signal processing device through wires
```
↓
```
Converting the original electro-cardio signals acquired by the electrode
into electro-cardio analog signals for output by the miniature
electro-cardio signal processing device; subjecting the electro-cardio
analog signals to bandpass filtering and signal amplification followed by
wavelet decomposition; reconstructing a filtered signal coefficient using a
wavelet decomposition structure to obtain denoised electro-cardio signals;
and transmitting the denoised electro-cardio signals to an infrared signal
transmitting device
```
↓
```
Transmitting the processed electro-cardio signals by the infrared
transmitting device to an infrared receiving device to complete the
real-time and miniaturized fish electro-cardio acquisition
```

FIG. 1

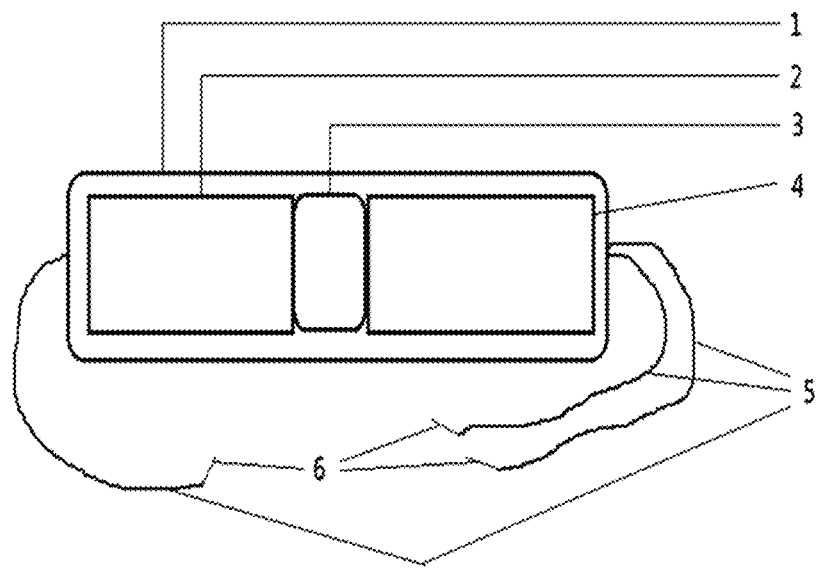

FIG. 2

METHOD AND SYSTEM FOR COMPREHENSIVE EVALUATION OF ORGANIC COMPOUND AND HEAVY METAL POLLUTION IN WATER BASED ON FISH ELECTROCARDIO

CROSS-REFERENCE TO RELATED APPLICATIONS

This application is a continuation of International Patent Application No. PCT/CN2019/072599, filed on Jan. 22, 2019, which claims the benefit of priority from Chinese Patent Applications No. 201810759036.6, filed on Jul. 11, 2018; No. 201811197187.3, filed on Oct. 15, 2018; No. 201811197170.8, filed on Oct. 15, 2018; No. 201811571919.0, filed on Dec. 21, 2018; and No. 201811572871.5, filed on Dec. 21, 2018. The contents of the aforementioned applications, including any intervening amendments thereto, are incorporated herein by reference in its entirety.

TECHNICAL FIELD

The present application relates to water quality evaluation, and more particularly to a method and system for comprehensive evaluation of organic compound and heavy metal pollution in a water based on fish electrocardio.

BACKGROUND OF THE INVENTION

With the transformation of the society and the modernization of industry and agriculture, a lot of environmental problems arise, such as the high occurrence of water pollution. The water pollution generally refers to water quality deterioration caused by the emission of a large number of toxic and harmful pollutants. It should be noted that the water pollution will greatly threaten the health and life safety of human beings and restrict the sustainable development of ecology and economy. Hence, it is of great significance to realize on-line monitoring and evaluation of water pollution.

Water pollution, caused by environmental pollutants such as organic compounds and heavy metals, has received great concern in society. The accumulation of environmental pollutants will lead to a teratogenic or carcinogenic effect in different organisms, which seriously influence the physiological mechanisms and functions of organisms, moreover, high concentration of pollutants may cause acute death to fish, invertebrates and algae. It has been found in some developing regions that the copper, lead and mercury concentrations in surface water reach 73 mg/L, 35 mg/L, and 1.14 ug/L, respectively, and other heavy metal pollutants such as manganese and chromium also seriously exceed the given standard. Therefore, the water environment safety and environment pollution control are generally concerned by society, and it is very important to achieve the monitoring of water quality.

At present, the methods for monitoring and analyzing water pollution mainly include test paper method, portable-instrument analysis and laboratory system analysis. The test paper method has large errors and is susceptible to the subjective judgment of the tester and changes of environmental parameters. The portable gas chromatography-mass spectrometry (GC-MS) can qualitatively detect the organic pollutants in the environment by combining the high resolution of gas chromatography with the strong qualification of mass spectrometer for molecules with different structures. For the voltammetry, a special electrode is necessary and the electrode needs to be frequently replaced in the actual measurement of heavy metal. In addition, the test results are susceptible to the base effect of a sample. Though the portable instrument shows strong specificity, it also has high cost. The laboratory system analysis can achieve comprehensive analysis of water pollutants, however, it fails to enable the real-time assessment of the water quality because it takes a long time in the process of water sampling-pretreatment-quality analysis, having difficulty in meeting the requirements of on-line monitoring for water pollution.

Thus, there is an urgent need to develop a method capable of on-line monitoring and evaluating the water pollution to timely and quickly assess water pollution and minimize the losses caused by sudden water pollution for economy, society and natural environment. In response to the needs of monitoring water pollution, more and more online bio-monitoring techniques have been developed and applied, including the methods based on biological indexes such as behavior and metabolism of aquatic organisms and fish electrocardio and electro-encephalo. However, the on-line monitoring techniques using behavior and metabolism as monitoring indexes have difficulties in determining the types of water pollutants. By contrast, fish electro-cardio analysis has been reported to have the potential to distinguish between organic pollutants and heavy metal pollutants. In the existing fish electro-cardio signal acquisition technology, the fish is required to be anesthetized and kept flat on a supporter for electro-cardio signal analysis, avoiding the collection of movement signals and the analysis errors. The existing methods, in which the fish is fixed by anesthesia for electro-cardio signal acquisition, have the following shortcomings.

First, the electrode is required to be connected with the electro-cardio acquisition and analysis instrument in the current methods for collecting fish electro-cardio signals to ensure the normal record, output and manual storage of the acquired electro-cardio signals, which limits the normal activities of fish in space. Specifically, the wires are limited in length and the circuit fails to be applied under water, and the smooth body surface make the fish not easy to fix, so that the acquisition instrument cannot be used on the fish or in the water just like the way that a portable electro-cardio measurer is used on human body, to collect the electro-cardio signals, failing to avoid the spatial limitation. Second, the pre-experimental anesthesia may affect the physiological and pathological characteristics of fish to a certain extent, such as heart rate, so the electro-cardio signals collected from fish under anesthesia fail to accurately reflect the normal physiological characteristics. In addition, the experimental fish is prone to death due to the lack of water and the fish cannot be maintained in a normal condition when placed flat on a laboratory bench, failing to accurately measure the electro-cardio signals.

Third, the existing methods cannot enable the long-term, real-time, on-line and continuous collection of fish electro-cardio since the fish out of water can only live for a short period, failing to accurately record and analyze the change of the electro-cardio signals over time. Therefore, in the case that the water quality changes are analyzed based on the fish electro-cardio, various electro-cardio parameters, such as changes in waveform, gap, heart rate, and heart rhythm, are required to be online collected and analyzed on the basis of the on-line collection of the fish electro-cardio signal base, so that the water quality can be online reflected by the specific changes of respective electro-cardio parameters. However, the existing electro-cardio acquisition techniques involving the use of anesthesia cannot online compare and analyze the water quality changes, so that they are rarely used in the water environment monitoring.

SUMMARY OF THE INVENTION

Given the shortcomings in the prior art, this application provides a method, device and system for miniaturized acquisition of fish electro-cardio to enable the long-term, continuous, real-time and on-line acquisition and analysis of fish electro-cardio signals when the fish to be detected is in a free state, where the miniaturized electro-cardio acquisition device can be carried on the fish. This application can perform the continuous, real-time and on-line acquisition for more than 30 days and can effectively ensure the real-time, validity and accuracy of the collected signals.

An aspect of the present disclosure provides a method for real-time acquisition of a fish electro-cardio using a miniaturized acquisition device.

An aspect of the present disclosure provides a real-time and miniaturized fish electro-cardio acquisition device, based on the above method for real-time acquisition of a fish electro-cardio using a miniaturized acquisition device.

An aspect of the present disclosure provides a real-time and miniaturized fish electro-cardio acquisition system, based on the real-time and miniaturized fish electro-cardio acquisition device.

An aspect of the present disclosure provides a method of monitoring water environment, based on the real-time and miniaturized fish electro-cardio acquisition system.

An aspect of the present disclosure provides a water environment monitoring system, based on the method of monitoring water environment.

An aspect of the present disclosure provides a method for determining a fish electro-cardio index in the assessment of organic pollution in water, based on the real-time and miniaturized fish electro-cardio acquisition system.

An aspect of the present disclosure provides a system for determining fish electro-cardio index in water organic pollution assessment, based on the method for determining a fish electro-cardio index in the assessment of water organic pollution.

An aspect of the present disclosure provides a method for assessing water organic pollution using a fish QT interval, based on the method for determining a fish electro-cardio index in the assessment of water organic pollution.

An aspect of the present disclosure provides a system for assessing water organic pollution using a fish QT interval, based on the method for assessing water organic pollution using a fish QT interval.

An aspect of the present disclosure provides a method for assessing water heavy metal pollution using a fish QRS interval, based on the real-time and miniaturized fish electro-cardio acquisition system.

An aspect of the present disclosure provides a system for assessing water heavy metal pollution using a fish QRS interval, and the system is operated based on the method for assessing water heavy metal pollution using a fish QRS interval.

An aspect of the present disclosure provides a method for online monitoring water sudden pollution based on fish electro-cardio, which is performed based on the real-time and miniaturized fish electro-cardio acquisition system.

An aspect of the present disclosure provides an on-line monitoring system for water sudden pollution based on fish electro-cardio, which is operated based on the method for online monitoring water sudden pollution based on fish electro-cardio.

An aspect of the present disclosure provides a computer-readable storage medium, in which a plurality of instructions are stored. These instructions are suitable to be loaded by a processor of a terminal device to perform the method for assessing water heavy metal pollution using a fish QRS interval, the method for assessing water organic pollution using a fish QT interval, and/or the method for online monitoring water sudden pollution based on fish electro-cardio.

An aspect of the present disclosure further provides a terminal device, which is further an internet terminal device, and the device includes a computer-readable storage medium for storing a plurality of instructions and a processor for executing the instructions; where the instructions are suitable to be loaded by the processor to perform the method for assessing water heavy metal pollution using a fish QRS interval, the method for assessing water organic pollution using a fish QT interval, and/or the method for online monitoring water sudden pollution based on fish electro-cardio.

BRIEF DESCRIPTION OF THE DRAWINGS

This application will be understandable with reference to the accompanying drawings constituting a part of this application. Exemplary embodiments and illustrations are intended to explain the present invention without limiting.

FIG. 1 is a flowchart of a method for real-time acquisition of fish electro-cardio using a miniaturized acquisition device according to one or more embodiments;

FIG. 2 is a schematic diagram of a real-time and miniaturized fish electro-cardio acquisition device according to one or more embodiments, in which: 1, waterproof housing; 2, battery; 3, infrared signal transmitting device; 4, miniature electro-cardio signal processing device; 5, wire; and 6, electrode;

DETAILED DESCRIPTION OF EMBODIMENTS

Figure 3:
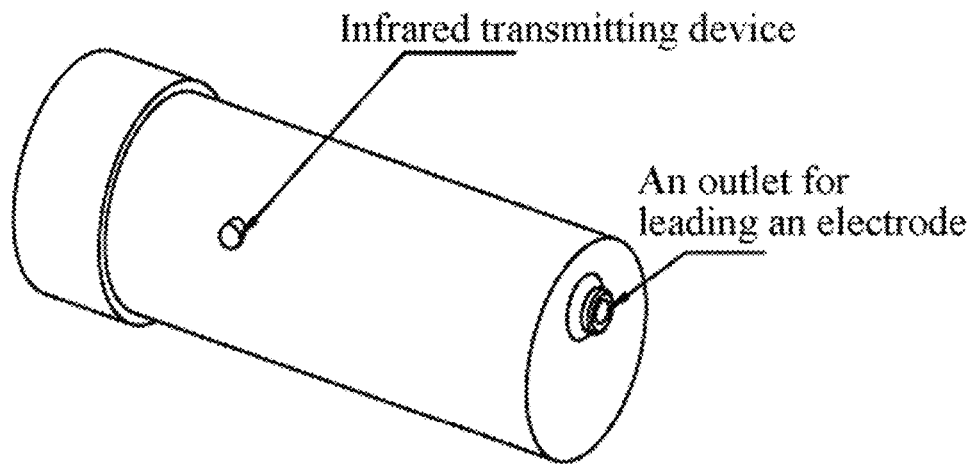
FIG. 3 is a schematic diagram of the waterproof housing according to one or more embodiments.

The technical solutions in the embodiments of the disclosure will be clearly and completely described below with reference to the accompanying drawings. It is apparent that the described embodiments are only a part of the embodiments of the present disclosure instead of all of the embodiments. All other embodiments obtained by those skilled in the art based on the embodiments of the disclosure without creative efforts, shall fall within the scope of the disclosure.

It should be noted that the following detailed description is illustrative and is intended to provide a further explanation of the application. Unless specified otherwise, all technical terms used in the embodiments have the same meanings as commonly understood by those skilled in the art to which this application pertains.

It should also be noted that the terms used herein are only intended to describe, but not limit the exemplary embodiments according to this application. As used herein, unless specified otherwise, the singular form is also intended to include plural forms, in addition, it should be understood that when the terms "comprise" and/or "include" are used in the specification, it is intended to indicate the presence of features, steps, operations, devices, components, and/or combinations thereof.

It should be noted that the flowcharts and block diagrams in the accompanying drawings illustrate the architecture, functionality, and operation that may be implemented in accordance with the method and system of each embodiment in this disclosure. It should be noted that each block of the flowcharts or block diagrams may represent a module, a program segment, or a portion of code, which may include one or more executable instructions for implementing the logic functions specified in each embodiment. It should also be noted that in some alternative implementations, the functions noted in the blocks may also occur in a different order than that illustrated in the drawings. For example, two blocks shown in succession may, in fact, be executed substantially in parallel, or sometimes in the reverse order, which depends on the functionality involved. It should also be noted that each block of the flowcharts and/or block diagrams, and combinations of blocks in the flowcharts and/or block diagrams can be implemented using a dedicated hardware-based system that performs the specified functions or operations, or can be implemented using a combination of dedicated hardware and computer instructions.

In the absence of conflict, features in the embodiments of the application may be combined with each other, and the present disclosure will be further described below in conjunction with the accompanying drawings and embodiments.

Given the shortcomings in the prior art, the problem to be solved is how to continuously acquire the fish electro-cardio signals on-line in real-time for a long time while ensuring that fish to be tested swims freely in a normal state in water. One or more embodiments of the disclosure provide a method, a device, and a system for miniaturizedly acquiring a fish electro-cardio in real time, realizing the miniaturization of an electro-cardio acquisition device worn by a fish to be tested while keeping the fish to be tested swimming in a normal state in water during the fish electro-cardio acquisition, and enabling continuous real-time on-line acquisition, so as to effectively ensure the real-time, validity and accuracy of the acquired electro-cardio signals.

A method for real-time acquisition of a fish electro-cardio using a miniaturized acquisition device is provided in one or more embodiments of the present disclosure, and a flowchart of the method is shown in FIG. 1, the method includes the steps as follows.

An electrode is inserted into a pericardial cavity of a fish to acquire signals and the acquired signals are transmitted to a miniature electro-cardio signal processing device through wires.

The miniature electro-cardio signal processing device converts the original electro-cardio signals acquired by the electrode into electro-cardio analog signals for output, and the electro-cardio analog signals are subjected to bandpass filtering and signal amplification followed by wavelet decomposition, and the filtered signal coefficient is reconstructed by a wavelet decomposition structure, then the denoised electro-cardio signals are obtained and transmitted to an infrared signal transmitting device.

The infrared signal transmitting device transmits the processed electro-cardio signals to the infrared signal receiving device to complete the real-time and miniaturized acquisition of fish electro-cardio.

An aspect of the present disclosure provides a real-time and miniaturized fish electro-cardio acquisition device, based on the above-described method for miniaturizedly acquiring a fish electro-cardio in real time, as shown in FIG. 2. The device includes a waterproof housing 2, which includes a body and a waterproof cover sealedly connected to the body.

A miniature electro-cardio signal processing device, a storage device connected to the miniature electro-cardio signal processing device, and a battery 1 are fixedly arranged in the body; the miniature electro-cardio signal processing device 4 is connected to an electrode 6 through wire 5; a bottom of the waterproof housing is provided with an outlet for leading the electrode, wherein the electrode 6 is inserted into a pericardial cavity of a fish to acquire the original electro-cardio signals which are then transmitted to the miniature electro-cardio signal processing device 4 for processing; and a side of the waterproof housing is provided with a through hole for placing an infrared signal transmitting device; a transmitting end of the infrared signal transmitting device passes through the through hole from an inside of the body of the waterproof housing and is sealedly connected to the through hole. The infrared signal transmitting device connects the battery and the miniature electro-cardio signal processing device, respectively, and transmits the processed electro-cardio signals to the infrared signal receiving device matched with the infrared signal transmitting device to complete the real-time electro-cardio signal acquisition of the fish.

The electro-cardio signals, acquired and emitted by the infrared signal transmitting device, can be transmitted through the aqueous phase and the gas phase to the infrared signal receiving device. The infrared signal transmitting device has a metal corresponding interface in contact with the battery, so as to connect the battery, thereby energizing the miniature electro-cardio signal processing device and the storage device connected to the processing device.

The wire connects to the miniature electro-cardio signal processing device, and is mainly used for transmitting signals, and departs from one end of the waterproof housing. There are three wires, and one end of respective wires is connected to one electrode. The wires are manufactured by coating a sheath on copper wire, where the sheath is made of a thermoplastic elastomer (TPE) rubber. The electrode is made of a silver fine needle having a diameter of 0.25 mm and having a needle tip for piercing into the pericardial cavity of the fish.

FIG. 3 is a schematic diagram of a waterproof housing in which a ratio of the diagram size to the physical size is 2:1. The housing cover is detachably screwed to the housing body.

Figure 4:
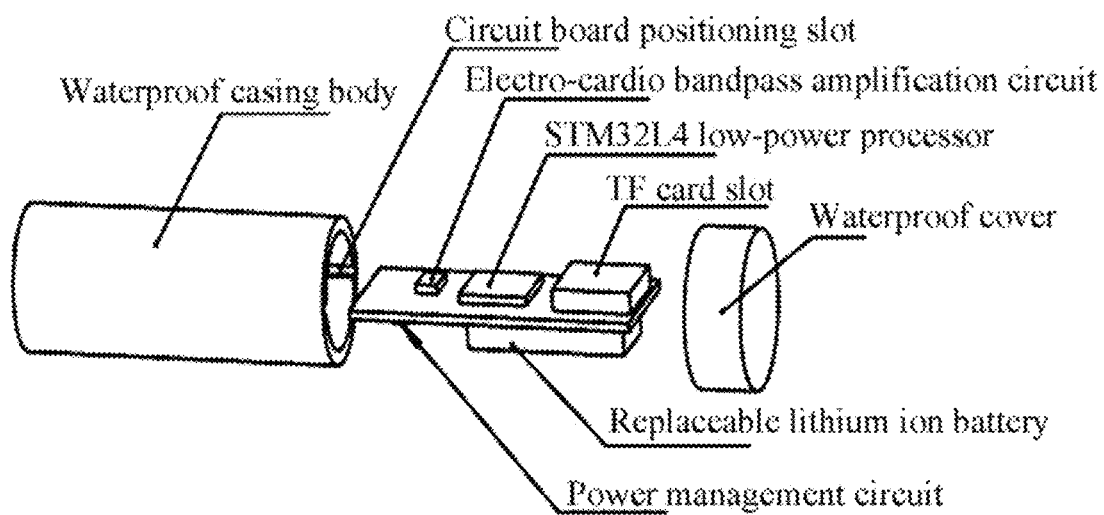
FIG. 4 is a schematic diagram showing the internal structure in the waterproof housing according to one or more embodiments.
Figure 5:
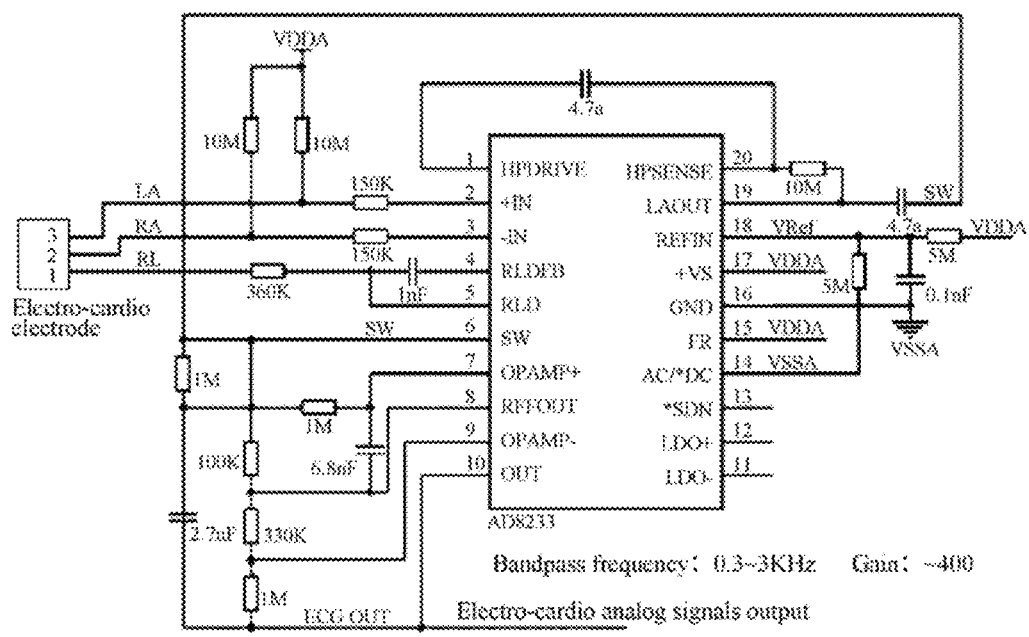
FIG. 5 is a schematic diagram of an electro-cardio acquisition circuit according to one or more embodiments.

FIG. 4 is a schematic diagram showing the internal structure in the waterproof housing in which a ratio of the diagram size to the physical size is 1:1, as shown in FIG. 4, and the miniature electro-cardio signal processing device includes an electro-cardio acquisition circuit, an electro-cardio bandpass amplifying circuit and a low-power consumption processor connected in sequence; the electro-cardio acquisition circuit is configured to convert the original electro-cardio signals acquired by the electrode into the electro-cardio analog signals for output. FIG. 5 is a schematic diagram of an electro-cardio acquisition circuit according to one or more embodiments, and an AD8233 chip and a fully integrated single-lead electrocardiogram (ECG) front end are adopted to convert the original electro-cardio signals acquired by the electro-cardio electrode into the electro-cardio analog signals for output. The electro-cardio bandpass amplifying circuit is configured to process the electro-cardio analog signals by bandpass filtering and signal amplification. The low-power consumption processor is configured to process the filtered and amplified electro-cardio signals by wavelet decomposition and reconstruct the filtered signal coefficient using a wavelet decomposition structure, thereby obtaining denoised electro-cardio signals; a STM32L4 low-power consumption processor is adopted.

The miniature electro-cardio signal processing device acquires the fish electro-cardio signals, and filters the interfering signals through filtering technology, and stores the filtered signals for a long time through the storage device, and the storage time can be more than 30 days, and the miniature electro-cardio signal processing device has the functions of acquiring, filtering and storing signals. The main technique of the filtering function is to obtain a wavelet decomposition by first using a zero-phase digital filter and then performing a 10-level one-dimensional wavelet analysis using coif5 wavelet. The filtered signal coefficient is further reconstructed by wavelet decomposition structure and coif5 wavelet. According to Stein's unbiased risk, soft threshold, electrical level noise level correlation estimation and the principle of 10-level coif5 wavelet, the denoised signals are finally obtained from the above reconstructed wavelet decomposition structure.

Figure 6:
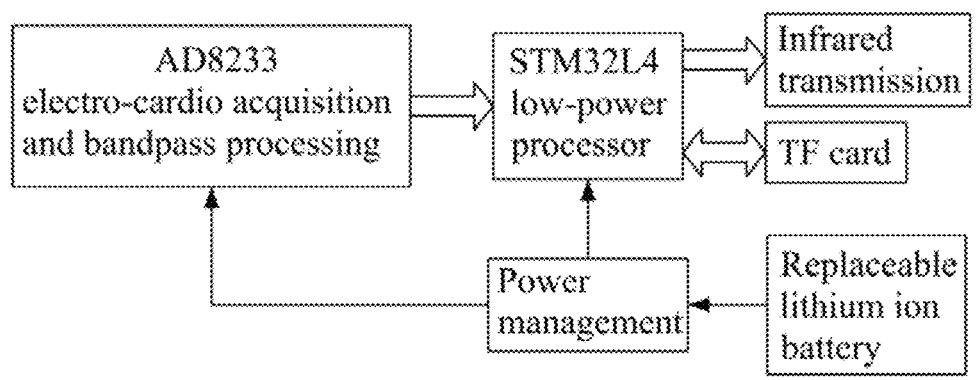
FIG. 6 is a schematic diagram of the real-time and miniaturized fish electro-cardio acquisition device according to one or more embodiments.

FIG. 6 is a schematic diagram showing the real-time and miniaturized fish electro-cardio acquisition device according to one or more embodiments.

The real-time and miniaturized fish electro-cardio acquisition device further includes a power management circuit; the battery is connected to the power management circuit and is respectively connected to the miniature electro-cardio signal processing device and the storage device through the power management circuit. The miniature electro-cardio signal processing device, the storage device, the power management circuit, and the battery are all provided on a circuit board; and two slots are symmetrically provided in the body for positioning the circuit board and the circuit board has a width equal to the spacing between the two slots. The waterproof housing, made of metal alloy, encapsulates the miniature electro-cardio signal processing device, the storage device sealedly connected to the processing device, the infrared signal transmitting device and the battery in threaded connection, facilitating the disassembly and replacement of the battery.

The miniaturized device of the disclosure is small and light, and is convenient for fish to carry on the fish; the device is fixed on the back of the fish, so that the fish can swim freely in a normal state in the water with the device, and the device can acquire, store and emit the electro-cardio signals of the fish in a normal state.

An aspect of the present disclosure provides a real-time and miniaturized fish electro-cardio acquisition system.

Figure 7:
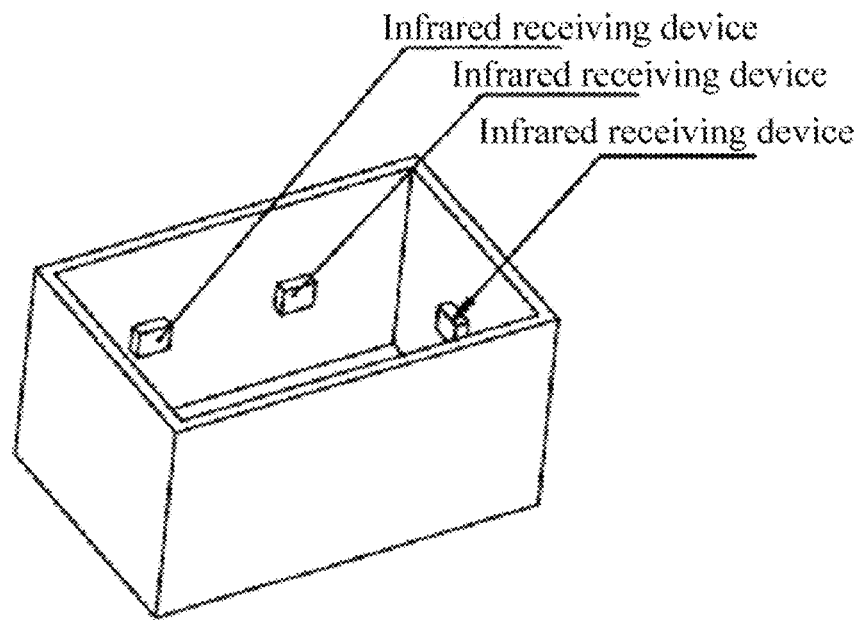
FIG. 7 is a schematic diagram of a real-time and miniaturized fish electro-cardio acquisition system according to one or more embodiments.

The system includes a real-time and miniaturized fish electro-cardio acquisition device worn by a fish and an infrared signal receiving device arranged on a water tank; where the infrared signal receiving device is used in conjunction with an infrared signal transmitting device provided in the real-time and miniaturized fish electro-cardio acquisition device. FIG. 7 shows the installation positions of the infrared signal receiving devices, and three thereof are respectively arranged on three sides of the water tank.

Given the shortcomings in the prior art, the problem to be solved is how to continuously acquire the fish electro-cardio signals on-line in real-time for a long time while ensuring that fish to be tested swims freely in a normal state in water. An aspect of the present disclosure provides a method, a device and a system for miniaturizedly acquiring a fish electro-cardio in real time, realizing the miniaturization of the electro-cardio acquisition device worn by the fish to be tested while keeping the fish to be tested swimming in a normal state in water during the fish electro-cardio acquisition, and enabling continuous real-time on-line acquisition, so as to effectively ensure the real-time, validity and accuracy of the acquired electro-cardio signals.

Figure 8:
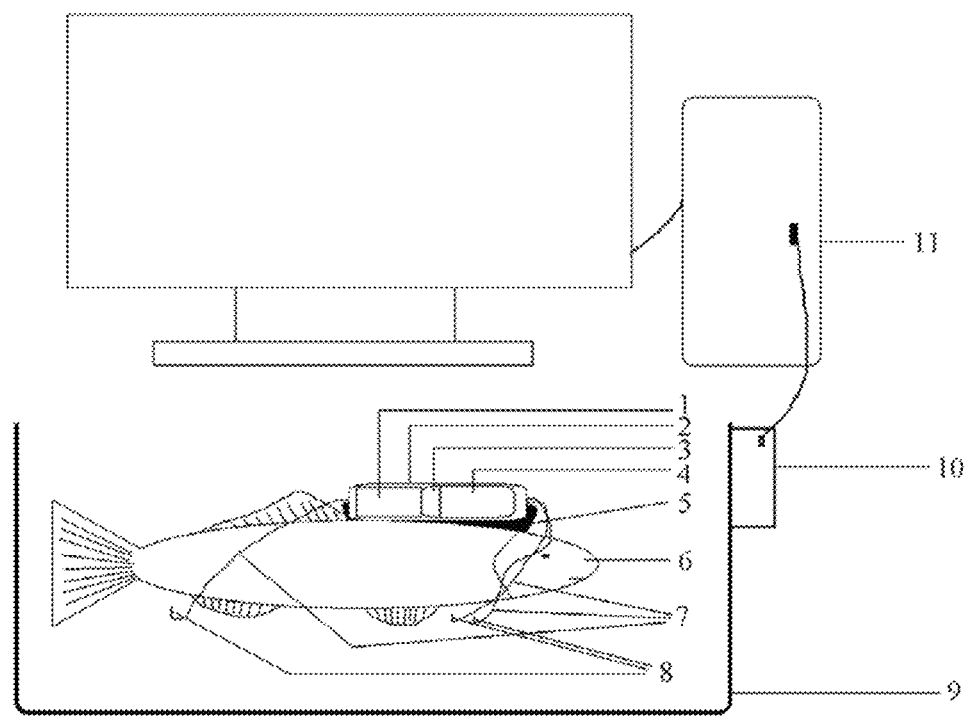
FIG. 8 is a schematic diagram of a water environment monitoring system based on the real-time and miniaturized fish electro-cardio acquisition system according to one or more embodiments, in which: 1, waterproof housing; 2, battery; 3, infrared signal transmitting device; 4, miniature electro-cardio signal processing device; 5, wire; 6, electrode; 7, carrier; 8, fish body; 9, water tank; 10, infrared signal receiving device; and 11, computer.
Figure 9:
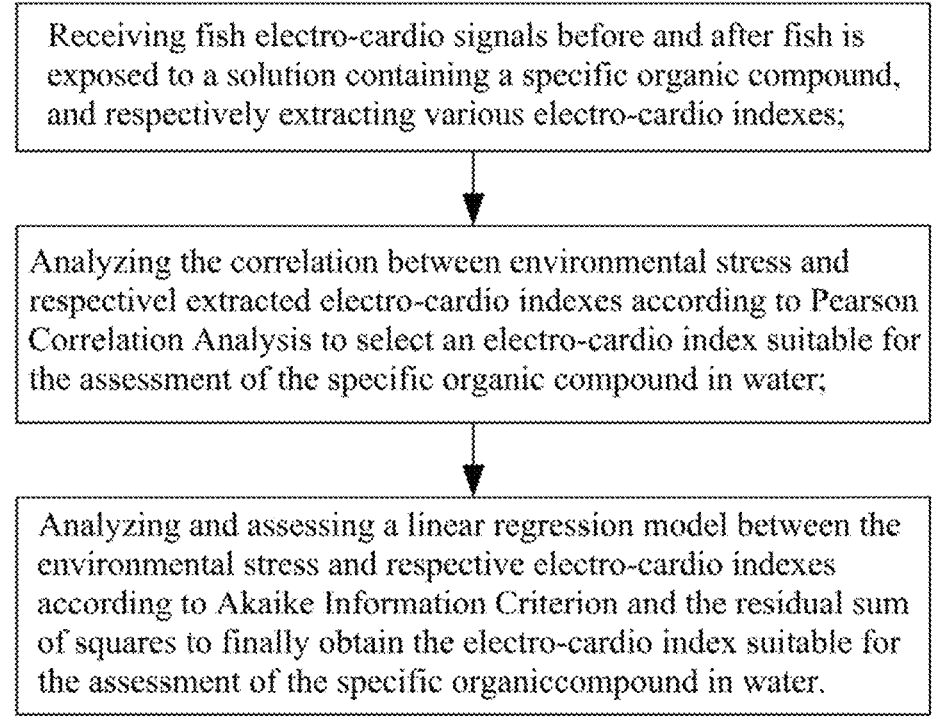
FIG. 9 is a flowchart of a method for determining fish electro-cardio index in the assessment of organic pollution in water according to one or more embodiments of the present disclosure.

FIG. 8 is a schematic diagram of a water environment monitoring system based on the structure of a real-time and miniaturized fish electro-cardio acquisition system suitable for the present embodiment. As shown in FIG. 8, a real-time and miniaturized fish electro-cardio acquisition system, which includes a real-time and miniaturized fish electro-cardio acquisition device 4 and an infrared signal receiving device 10;

the real-time and miniaturized fish electro-cardio acquisition device 4 is arranged on the fish body 8 through a carrier 7 matching with a profile of the fish; and the carrier is configured to ensure that the carrier and the real-time and miniaturized fish electro-cardio acquisition device as a while are equal in gravity and buoyancy, since the carrier is made of a low-density material. In this embodiment, the carrier is saddle-shaped made of the low-density material, and is hand-made according to the shape of the device, after the carrier fits with the device, the combination can be placed in the water without sinking or floating, achieving the equal state of the gravity and the buoyancy, avoiding the load on the fish and ensuring that the fish swims in a normal state. The real-time and miniaturized fish electro-cardio acquisition device 4 is fixed on the back of the fish, so that the fish can freely swim in a normal state in the water with the device without load added.

The real-time and miniaturized fish electro-cardio acquisition device includes a waterproof housing 2, where a miniature electro-cardio signal processing device, a storage device connected to the miniature electro-cardio signal processing device, and a battery 1 are fixedly arranged in the waterproof housing. The miniature electro-cardio signal processing device 4 is connected to the electrode 6 through wire 5; an outlet for leading the electrode is provided at a bottom of the waterproof housing; the electrode 6 is inserted into the pericardial cavity of the fish to acquire the original electro-cardio signals which are then transmitted to the miniature electro-cardio signal processing device through wires for processing;

a side of the waterproof housing is provided with a through hole for placing the infrared signal transmitting device; a transmitting end of the infrared signal transmitting device passes through the through hole from an inside of the body of the waterproof housing and is sealedly connected to the through hole. The infrared signal transmitting device connects the battery and the miniature electro-cardio signal processing device, respectively, and transmits the processed electro-cardio signals to the infrared signal receiving device matched with the infrared signal transmitting device to complete the real-time electro-cardio signal acquisition of the fish. The electro-cardio signals, acquired and transmitted by the infrared signal transmitting device, can be transmitted through the aqueous phase and the gas phase to the infrared signal receiving device. The infrared signal transmitting device has a metal corresponding interface in contact with the battery, so as to connect the battery, thereby energizing the miniature electro-cardio signal processing device and the storage device connected to the processing device.

The infrared signal receiving device is provided on the side wall of the water tank for receiving the processed electro-cardio signals. As shown in FIG. 7, the infrared signal receiving device includes a first infrared signal receiving device, a second infrared signal receiving device, and a third infrared signal receiving device, which are respectively distributed on three side walls of the water tank.

The miniaturized device of the disclosure is small and light, and is convenient for fish to carry on the fish; the device is fixed on the back of the fish, so that the fish can swim freely in a normal state in the water with the device which can acquire, store and emit the electro-cardio signals of the fish in a normal state.

An aspect of the present disclosure provides a method of monitoring water environment, and the method includes the following steps.

A real-time fish electro-cardio signals in a certain period of time acquired by a real-time and miniaturized fish electro-cardio acquisition system are received to monitor a water environment.

A water environment monitoring system is based on the real-time and miniaturized fish electro-cardio acquisition system and computer 11; where the computer is configured to receive real-time fish electro-cardio signals in a certain period of time acquired by a real-time and miniaturized fish electro-cardio acquisition system to monitor the water environment.

In the present embodiment, a deltamethrin organic pesticide pollutant in water is illustrated as an example. The deltamethrin is an important pyrethroid organic pesticide pollutant in aquatic ecosystems. Pyrethroid organic pesticides may adversely affect or even kill aquatic organisms, moreover, have more obvious toxic effects on fish and some aquatic invertebrates under experimental conditions. Deltamethrin has a certain effect on the sodium current of cardiomyocytes, and further causes decreased cardiac activity. Moreover, deltamethrin also has a certain effect on cardiac function and atrial contractility, which can cause arrhythmia. Biomonitoring has the advantages of high sensitivity, low cost, convenient management and rich biodiversity. Many organisms, such as algae, daphnia, large invertebrates and fish, are sensitive to environmental toxicants. Biomonitoring can directly and continuously detect various pollutants and toxic effects based on the physiology and behavior of the organism. At the same time, the biological water quality monitoring has low cost in monitoring and maintenance. Biological monitoring can adapt to environmental conditions over time. Through reasonable and scientific assessment of the data obtained through water quality monitoring, scientific and effective planning and regulation can be formulated, and effective and reasonable measures can be taken.

In order to accurately monitor the water quality of the water environment, more and more researchers use organisms to assess and monitor the water quality environment. There are many methods and assessment indexes for biological water quality monitoring, however, using electro-cardio indexes as indexes to assess water quality is rarely achievable. In addition, most biological water quality monitoring methods are complex and difficult to implement. Therefore, it is necessary to develop a practicable biological water quality monitoring methods.

First, the fish electro-cardio index in the water quality assessment needs to be determined.

Figure 10:
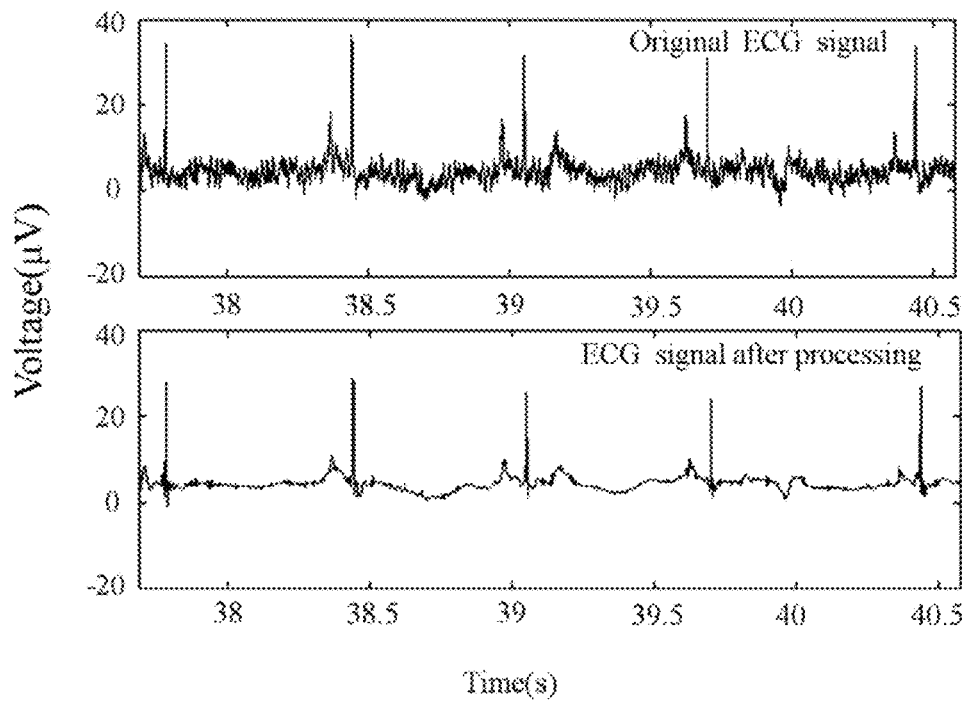
FIG. 10 shows fish electrocardiogram acquired before and after pre-processing according to one or more embodiments of the present disclosure.

As shown in FIG. 10, illustrated is a method for determining a fish electro-cardio index in the assessment of water organic pollution.

The method bases on the real-time and miniaturized fish electro-cardio acquisition system, and the method includes the following steps.

Fish electro-cardio signals respectively before and after the fish is exposed to a solution containing a specific organic compound are gathered by the real-time and miniaturized fish electro-cardio acquisition system, and various electro-cardio indexes are respectively extracted.

The correlation between environmental stress and respective extracted electro-cardio indexes is analyzed according to Pearson Correlation Analysis to select an electro-cardio index suitable for the assessment of water quality with respect to this specific organic compound.

A linear regression model between the environmental stress and respective electro-cardio indexes is analyzed and assessed according to Akaike Information Criterion and the sum of square error to finally obtain an electro-cardio index suitable for the assessment of water quality with respect to the specific organic compound.

It should be noted that, in the method, the extracted electro-cardio indexes include P-wave amplitude, Q-wave amplitude, R-wave amplitude, S-wave amplitude, T-wave amplitude and P-R interval, QRS interval, S-T interval, and Q-T interval.

In the present method, the real-time electro-cardio signals were acquired from multiple fishes respectively exposed to different concentrations of the specific organic compound. Firstly, the zebrafish was exposed to an organic solvent deltamethrin solution. The 48 h medial lethal concentration of deltamethrin for zebrafish was 5.2 μg/L, which was recorded as 1 toxic unit (1 TU). The zebrafish was exposed to deltamethrin in different concentrations, respectively 0.52 μg/L, 2 μg/L and 2.6 μg/L (0.1 TU, 0.38 TU and 0.5 TU). Three zebrafishes were used in each exposed group.

The acquired electro-cardiographs were subjected to filtering and interference removal to become clearer; the analyzed data was processed, and then was analyzed by Matlab software and SPSS software to estimate the electro-cardio changes based on data differences.

Figure 11:
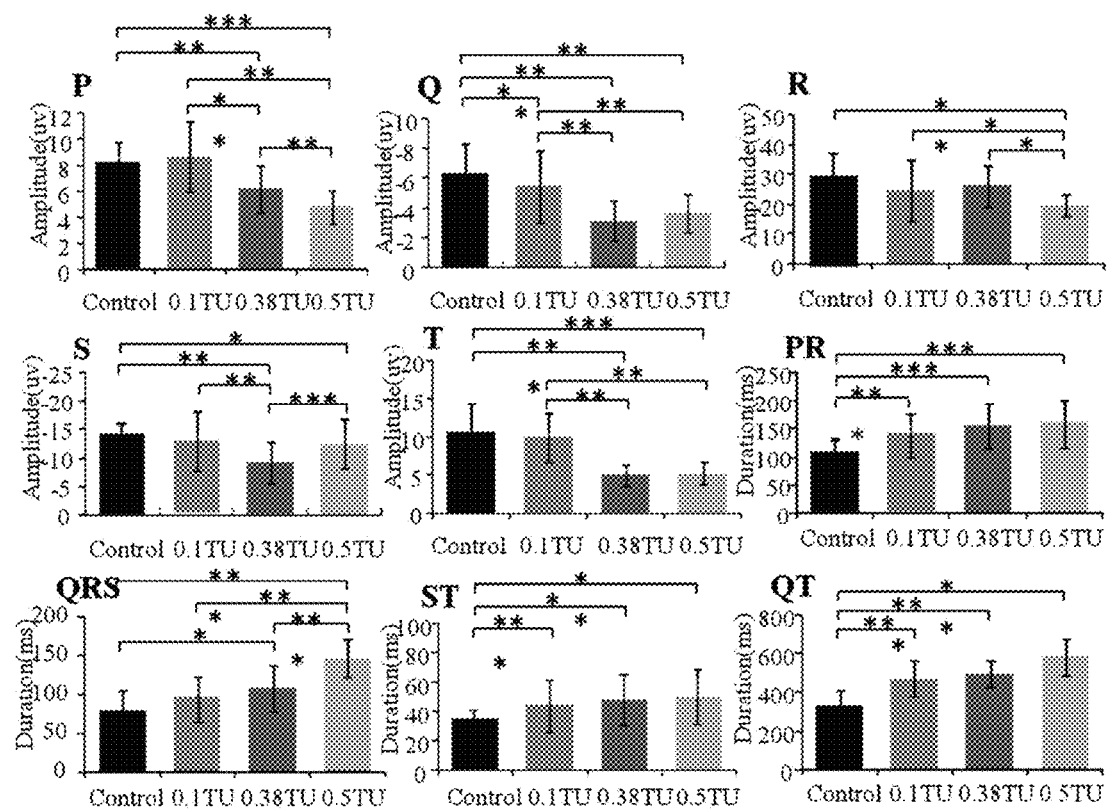
FIG. 11 is a schematic diagram showing the effects of different concentrations of deltamethrin on various electro-cardio indexes of zebrafish according to one or more embodiments of the present disclosure.

The acquired electro-cardiogram, as shown in FIG. 11, were subjected to filtering and interference removal to become clearer.

Figure 12:
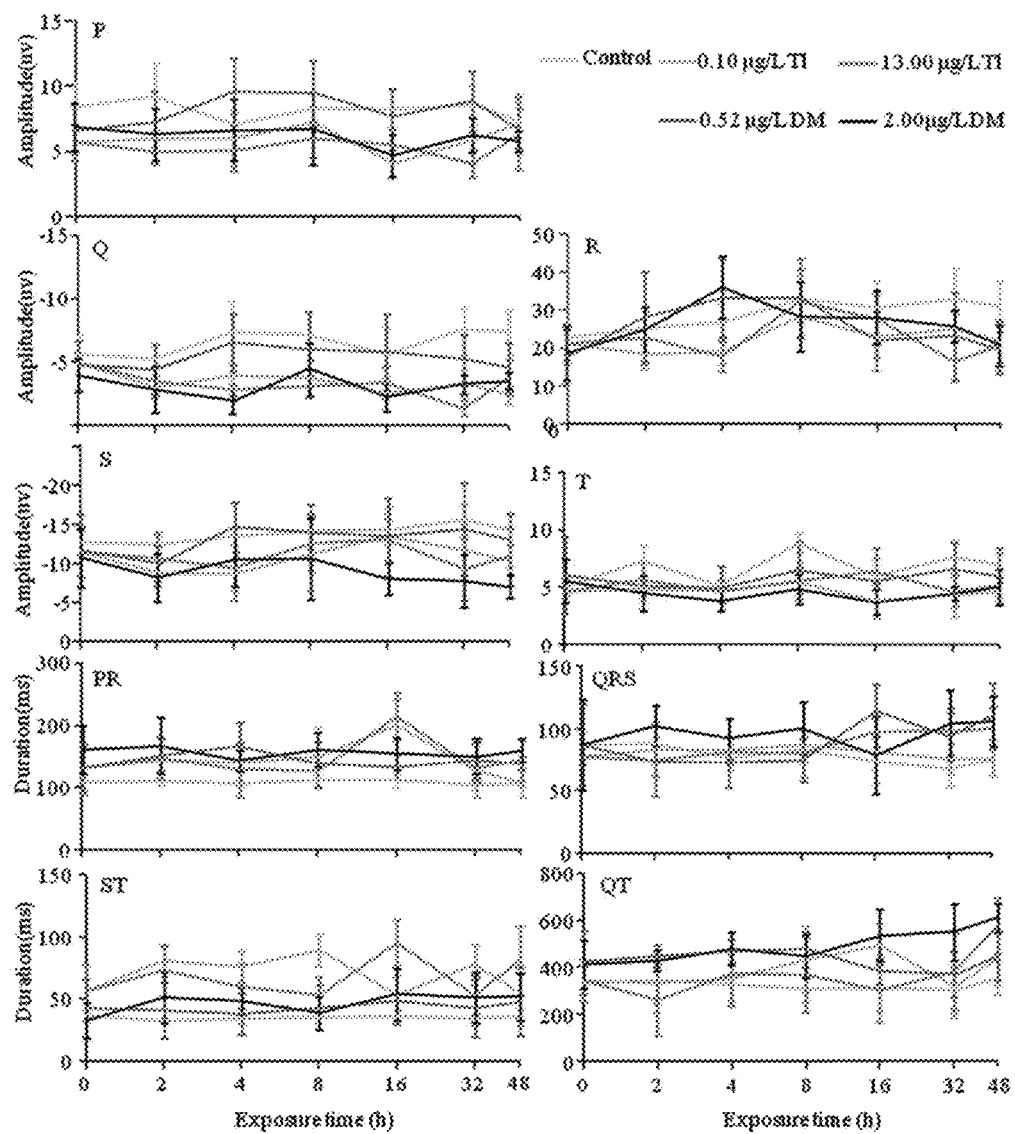
FIG. 12 is a schematic diagram showing the effect of deltamethrin in various concentrations at different time points on each electro-cardio index of zebrafish according to one or more embodiments of the present disclosure.
Figure 13:
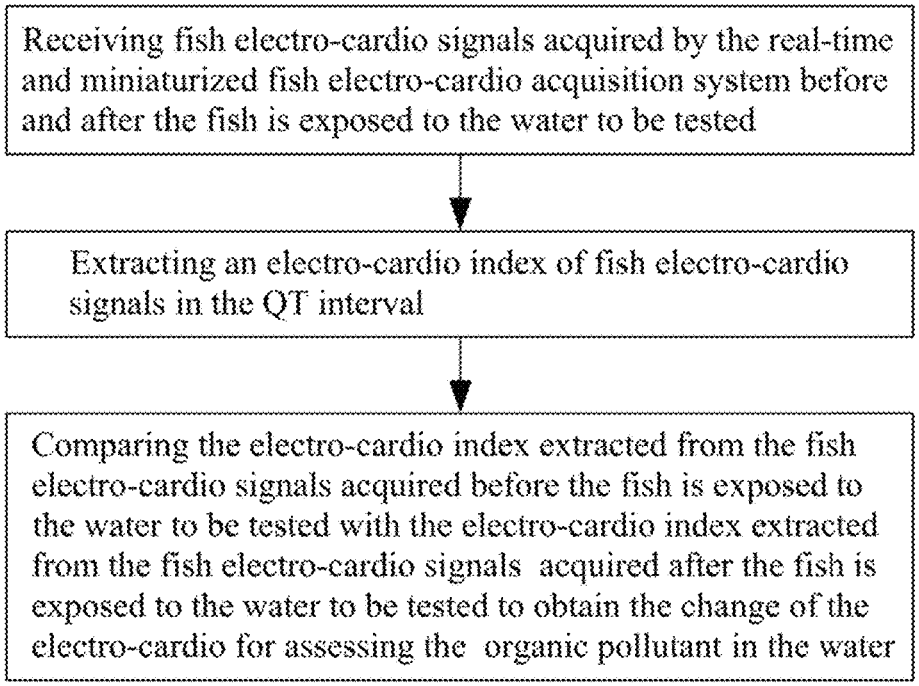
FIG. 13 is a flowchart of a method for assessing water organic pollution based on fish QT interval according to one or more embodiments of the present disclosure.

The electro-cardio signal data acquired in real-time at specific points (0 h, 2 h, 4 h, 8 h, 16 h, 32 h, 48 h) was analyzed, and the analysis showed that, the electro-cardio parameters of the zebrafish changed as the concentration of deltamethrin increased, such as the amplitudes of P-wave, Q-wave, R-wave, S-wave and T-wave decreased, however, the PR interval, QRS interval, ST interval and QT interval increased, as shown in FIGS. 11-12. The asterisks in FIG. 11 represent significance of correlation and were obtained through the analysis of Matlab software.

The host collects 9 electro-cardio indexes, including P-wave amplitude, Q-wave amplitude, R-wave amplitude, S-wave amplitude, T-wave amplitude and P-R interval, QRS interval, S-T interval, and Q-T interval from the received fish electro-cardio signals to analyze the changes of the electro-cardio indexes respectively before and after the fish is exposed to the water to be tested. If there is any change, it indicates that the water to be tested harms the fish electro-cardio; if there is no change, it indicates that the water to be tested has no or little effect on the fish electro-cardio.

In the electro-cardio indexes, Pearson correlation is used in SPSS to perform correlation analysis between environmental stress (E) and each electro-cardio index to determine the electro-cardio index for water quality assessment (Pearson correlation coefficient r is closer to 1, the better the correlation, the smaller the p-value, the more significant the correlation, $p<0.05$ means being significant, $p<0.01$ means being very significant, $p<0.001$ means being extremely significant); where the environmental pressure E is related to the pollutant concentration and time. Then, through Akaike Information Criterion (AIC) and based on the sum of square error (SSE), the linear regression model between E and each electrocardiogram parameter is analyzed and assessed (where the SSE in the linear regression model is smaller, and the AIC value is smaller, the better the model fits).

In one or more embodiments of the present disclosure, correlation analysis between QT interval and environmental pressure (E) based onlinear regression showed that P-waves and R-waves were significantly correlated with E caused by deltamethrin (correlation coefficients were $r=0.492$, $p=0.032<0.05$; $r=0.495$, $p=0.031<0.05$, respectively), and the QT interval was very significantly correlated with E, where correlation coefficient $r=0.789$ and the related significance $p<0.001$, which indicates that the QT interval was very significantly correlated to E caused by the organic pollutant deltamethrin. Then, through the AIC and based on SSE, the linear regression model between E and each electrocardiogram parameter was further analyzed and assessed. According to the data analysis, among the linear regression models established by QT interval, $R^2$ value is largest, SSE is smallest and AIC value is smallest. In this case, it can be concluded that the QT interval can be used as an index in the deltamethrin stress assessment. Therefore, organic pollutant in water quality can be monitored by studying and analyzing QT intervals.

Figure 14:
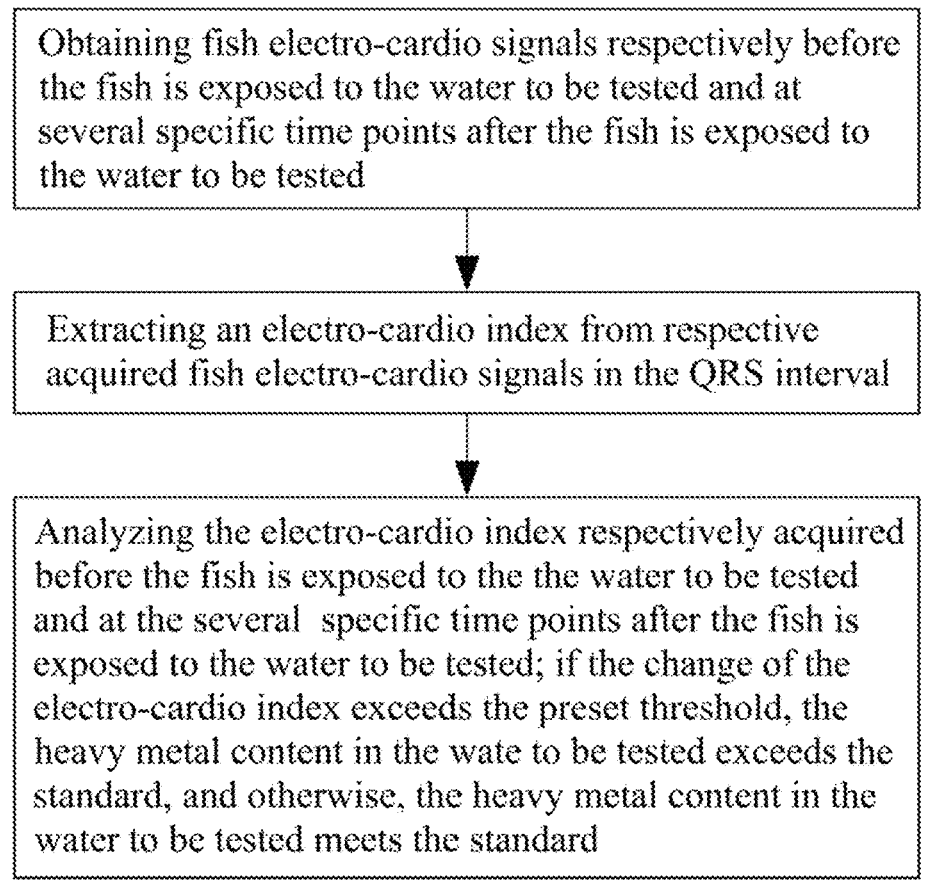
FIG. 14 is a flowchart of a method for assessing water heavy metal pollution based on fish QRS interval according to one or more embodiments of the present disclosure.

As shown in FIG. 14, provided is a method for assessing water organic pollution using a fish QT interval, which is based on the method for determining a fish electro-cardio index in the assessment of water quality in one or more the embodiments above, and the method includes the following steps.

Fish electro-cardio signals respectively before and after the fish is exposed to the water to be tested acquired by the real-time and miniaturized fish electro-cardio acquisition system are received.

An electro-cardio index of the fish electro-cardio signals in the QT interval is extracted.

The electro-cardio index extracted from the fish electro-cardio signals respectively acquired before and after the fish is exposed to the water to be tested are compared to obtain the change of the interval electro-cardio index, thereby determining an organic pollutant in the water to be tested.

Further, in the method, fish electro-cardio signals are pre-processed, where the pre-processing includes filtering and interference removal.

An aspect of the present disclosure further provides a system for assessing water organic pollution using a fish QT interval, which is operated based on the method for assessing water organic pollution using a fish QT interval, and the system includes a real-time and miniaturized fish electro-cardio acquisition system and a computor terminal.

The computor terminal with a computer host, processes data mainly through MATLAB software. The system is capable of acquiring electro-cardio signals more stable. The acquired electrocardiograms are subjected to filtering and interference removal to obtain clearer electrocardiograms; then the electrocardiogram is analyzed through system software to process the analyzed data. The electro-cardio indexes are analyzed on the changes respectively before and after the fish is exposed to the water to be tested. If there is any change, it proves that the water to be tested harms the fish electro-cardio; otherwise, it proves that the water to be tested has no or little effect on the fish electro-cardio.

Figure 15:
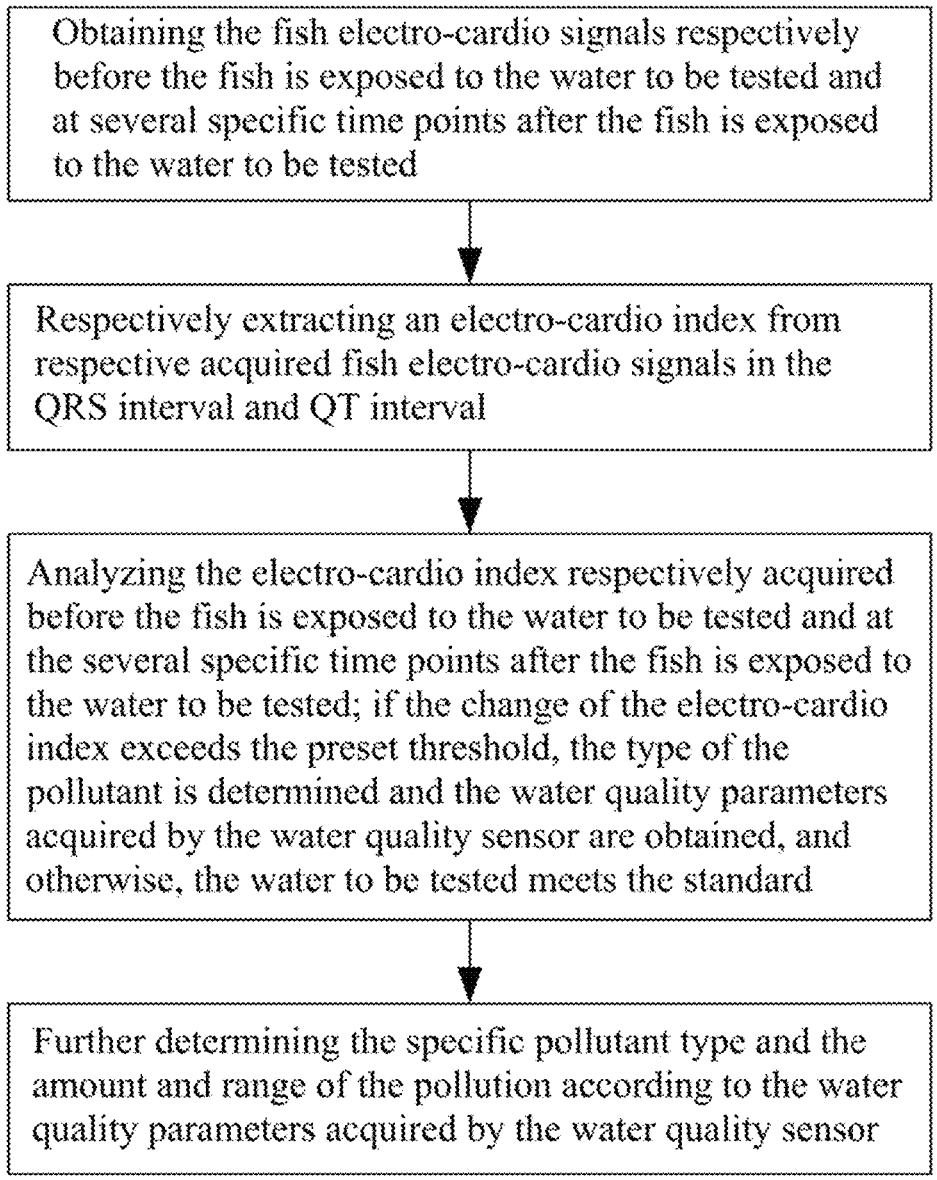
FIG. 15 is a flowchart of a method for online monitoring water sudden pollution based on fish electro-cardio according to one or more embodiments of the present disclosure.

An aspect of the present disclosure provides a method of assessing water heavy metal pollution using a fish QRS interval, as shown in FIG. 15, and the method includes the following steps.

The fish electro-cardio signals acquired by the real-time and miniaturized fish electro-cardio acquisition system are obtained before the fish is exposed to the water to be tested and at several specific time points after the fish is exposed to the water to be tested.

An electro-cardio index of the acquired electro-cardio signals of respective fish in the QRS interval is extracted.

A change of the electro-cardio index is analyzed before the fish is exposed to the water to be tested and at several specific time points after the fish is exposed to the water to be tested; if the change exceeds a preset threshold, the heavy metal content of the water to be tested exceeds the standard, otherwise, the heavy metal content of the water to be tested meets the standard.

Further, in the method, the fish electro-cardio signals of multiple fishes are acquired respectively before the fishes are exposed to the water to be tested and at several specific time points after the fishes are exposed to the water to be tested.

Further, in the method, the fish electro-cardio signals are pre-processed, where the pre-processing includes filtering and interference removal.

An aspect of the present disclosure provides a system for assessing water heavy metal pollution by fish QRS interval, which is operated based on the method for assessing water heavy metal pollution using a fish QRS interval. The system includes a real-time and miniaturized fish electro-cardio acquisition system, an infrared signal receiving device and a computor terminal.

The real-time and miniaturized fish electro-cardio acquisition system is provided on a fish through a carrier matching with a profile of the fish; and the carrier is configured to ensure that the carrier and the real-time and miniaturized fish electro-cardio acquisition device as a whole are equal in gravity and buoyancy.

The real-time and miniaturized fish electro-cardio acquisition device includes a waterproof housing, in which a miniature electro-cardio signal processing device, a storage device connected to the miniature electro-cardio signal processing device, and a battery are fixedly arranged. The miniature electro-cardio signal processing device is connected to an electrode through wires; a bottom of the waterproof housing is provided with an outlet for leading the electrode; the electrode is inserted into a pericardial cavity of the fish to acquire the original electro-cardio signals which are then transmitted through wires to the miniature electro-cardio signal processing device for processing; a through hole for placing the infrared signal transmitting device is provided on a side of the waterproof housing, and a transmitting end of the infrared signal transmitting device passes through the through hole from an inside of the body of the waterproof housing and is sealedly connected to the through hole. The infrared signal transmitting device is connected to the battery and the miniature electro-cardio signal processing device, respectively and transmits the processed electro-cardio signals to the infrared signal receiving device matched with the infrared signal transmitting device to complete the real-time electro-cardio signal acquisition of the fish.

The infrared signal receiving device is provided on a side wall of water tank for receiving the processed electro-cardio signals and transmitting the received signals to the computor terminal.

Further, the electrode of the system includes an acquisition electrode and a reference electrode, where the acquisition electrode is embedded in the pericardial cavity of the fish which is used for electro-cardio signal acquisition, and the reference electrode is embedded near the cloacal orifice of the fish which is used for electro-cardio signal acquisition; and the acquisition electrode and the reference electrode embedded share the same length in the fish.

An aspect of the present disclosure provides a method for determining a fish electro-cardio index for assessing water heavy metal pollution, which is based on the system for assessing water heavy metal pollution by fish QRS interval, and the method includes the following steps.

The fish electro-cardio signals are obtained by the real-time and miniaturized fish electro-cardio acquisition system respectively before and after the fish is exposed to a solution containing specific heavy metal, and various electro-cardio indexes are respectively extracted.

The correlation between environmental stress and each extracted electro-cardio index is analyzed according to Pearson Correlation Analysis, electro-cardio indexes used for assessing the water heavy metal are filtered.

A linear regression model between the environmental stress and respective electro-cardio indexes is analyzed and assessed according to Akaike Information Criterion and the sum of square error to finally obtain an electro-cardio index suitable for the assessment of water with respect to the heavy metal.

Further, in the method, the electro-cardio signals are acquired at different specific time points from multiple fishes respectively exposed to different concentration of different heavy metals.

Further, in the method, the extracted electro-cardio indexes include P-wave amplitude, Q-wave amplitude, R-wave amplitude, S-wave amplitude, T-wave amplitude and P-R interval, QRS interval, S-T interval, and Q-T interval.

Further, in the method, the fish electro-cardio signals are pre-processed, where the pre-processing includes filtering and interference removal.

Further, in the method, before the fish electro-cardio signal processing, the acquired fish electro-cardio signals are processed by the on-line acquisition and analysis system of fish electro-cardio.

Further, in the method, before the analysis of the correlation between the environmental stress and each extracted electro-cardio index according to the Pearson correlation analysis method, the impact trend of the concentration variation of the specific heavy metal and the various time points on the fish electro-cardio indexes is determined.

Further, a significant correlation is determined through this method between the QRS interval in the fish electro-cardio indexes and the stress of heavy metal in the water so that the QRS interval is suitable for assessing water quality with respect to the heavy metal.

The method acquires electro-cardio mainly through multi-channel physiological signal acquisition systems, then the acquired electro-cardio signals are preliminarily processed to obtain data, then through software processing, water quality is further assessed. Biomonitoring can directly and continuously detect various pollutants and toxic effects based on the physiology and behavior of the organism. At the same time, biological water quality monitoring has low cost in monitoring and maintenance. Biological monitoring can adapt to environmental conditions over time. Biological monitoring can be realized by various methods, however, using electro-cardio parameters as assessment indexes is rarely achieved.

The water environment is assessed by the method as follows: through the on-line acquisition and analysis system of fish electro-cardio, the electro-cardio signals are respectively acquired before and after the fish is exposed to the water to be tested, and 9 indexes are extracted, including: the amplitudes of P-wave, Q-wave, R-wave, S-wave and T-wave, and P-R interval, QRS interval, S-T interval and Q-T interval. The analysis is performed on the changes of the electro-cardio indexes respectively before and after the fish is exposed to the water to be tested. If there is any change, it proves that the water to be tested harms the fish electro-cardio. If there is no change, it proves that the water to be tested has no or little effect on the fish electro-cardio.

Correlation analysis of QRS interval and E upon linear regression showed that P-wave and R-wave were significantly correlated with E caused by copper, lead, mercury, manganese and chromium, respectively, indicating that the QRS interval is related to E.

Then, further, through AIC and based on SSE, the linear regression model between E and each electrocardiogram parameter was analyzed and assessed. According to the data analysis, among the linear regression models established by the QRS interval, $R^2$ value was largest, SSE was smallest and AIC value was smallest. In this case, it can be concluded that the QRS interval can be used as an index in the copper, lead, mercury, manganese, and chromium stress assessment. Among the electro-cardio parameters, tissue mapping showed that, in the stress of heavy metals such as copper, lead, mercury, manganese, chromium and all electro-cardio parameters of classified data patterns, QRS was very similar to E, indicating that the QRS interval is related to E. Correlation analysis between QRS interval and environmental stress based onlinear regression showed that correlation coefficient r=0.729 and related significance p<0.01, which proves a very significant correlation. In this case, it can be concluded that the QRS interval can be used as an index for stress assessment of heavy metals such as copper, lead, mercury, manganese, and chromium.

This indicates that the QRS interval is directly related to the environmental stress E. The specification and assessment of ECG parameters in heavy metal pollution indicate that there is a significant correlation between QRS complex and heavy metal stress, where r value is highest and p is smallest among all ECG features. In this case, it can be concluded that the QRS interval can be used as an index of heavy metal stress assessment.

A specific technical solution according to one or more embodiments of the present disclosure was as follows. Firstly, the koi was exposed to a copper sulfate solution, and a 48 h semi-lethal concentration of copper sulfate for the koi was 10.3 mg/L, which was recorded as 1 toxic unit (1 TU). The koi was exposed to copper sulfate in different concentrations, respectively 1.3 mg/L, 5.15 mg/L (0.1 TU, 0.5 TU) and 1 mg/L. The acquisition of the koi electro-cardio signals was performed. The electro-cardio signal acquisition memory and the saddle-shaped carrier were fixed on the back of the fish, enabling that the fish can swim freely in the normal state in the water with the device, without load added. Then 3 sets of parallel experiment were performed to obtain the experimental results of electro-cardio signals which were subjected to the treatment and analysis of the electro-cardio indexes.

Mercury, cadmium and manganese have the same technical solution as the copper sulfate, and the same experimental steps were as follows. A 48 h semi-lethal concentration of mercury chloride solution for koi was 0.13 mg/L, which was recorded as 1 toxicity unit (1 TU). Koi was exposed to the mercury chloride solution in different concentrations, respectively, 0.013 mg/L, 0.065 mg/L (0.1 TU, 0.5 TU) and 0.05 ug/L. The acquisition of the koi electro-cardio signals was performed. The electro-cardio signal acquisition memory and the saddle-shaped carrier were fixed on the back of the fish, enabling that the fish can swim freely in the normal state in the water with the device, without load added. 3 sets of parallel experiments were performed to obtain the experimental results of electro-cardio signals which were subjected to the treatment and analysis of the electro-cardio indexes.

A 48 h semi-lethal concentration of the cadmium chloride solution for Koi was 23.6 mg/L, which was recorded as 1 toxic unit (1 TU). The koi was exposed to hexavalent chromium solution in different concentrations, respectively, 2.36 mg/L, 11.8 mg/L (0.1 TU, 0.5 TU) and 0.05 mg/L. The acquisition of the koi electro-cardio signals was performed. The electro-cardio signal acquisition memory and the saddle-shaped carrier were fixed on the back of the fish, enabling that the fish can swim freely in the normal state in the water with the device, without load added. 3 sets of parallel experiments were performed to obtain the experimental results of electro-cardio signals which were subjected to the treatment and analysis of the electro-cardio indexes.

A 48 h semi-lethal concentration of manganese solution for koi was 2.75 mg/L, which was recorded as 1 toxic unit (1 TU). The koi was exposed to manganese solution in different concentrations, respectively, 0.275 mg/L and 1.375 mg./L (0.1 TU, 0.5 TU) and 0.1 mg/L. The acquisition of koi electro-cardio signals was performed. The electro-cardio signal acquisition memory and the saddle-shaped carrier were fixed on the back of the fish, enabling that the fish can swim freely in the normal state in the water with the device, without load added, and 3 sets of parallel experiments were performed to obtain experimental results of electro-cardio signals which were subjected to the treatment and analysis of the electro-cardio indexes.

The koi electro-cardio was acquired and measured by a system of on-line electro-cardio acquisition. The acquired electrocardiograms were subjected to filtering and interference removal to become clearer, as shown in FIG. 11; then the electrocardiograms were analyzed by Matlab and SPSS, and the analyzed data is processed. The analysis was performed on the changes of the electro-cardio indexes respectively before and after the fish is exposed to the water to be tested. If there is any change, it indicates that the water to be tested harms the fish electro-cardio; if there is no change, it indicates that the water to be tested has no or little effect on the fish electro-cardio.

According to one or more embodiments of the present disclosure, there is a significant correlation between QRS intervals and heavy metal pollutants stress. Water heavy metal pollutants can be monitored by studying and analyzing the QRS intervals.

The water quality can be monitored in real-time based on the fish electro-cardio analysis, so as to timely pre-warn and assess water sudden pollution accidents, thereby minimizing the loss of the economy and the natural environment. In order to overcome the problems that the water quality cannot be monitored in real-time and water sudden pollution accidents can not be assessed on-line in the prior art, the present application provides a real-time continuous on-line electro-cardio acquisition device while keeping fish swimming in a normal state and a method for using the above device as a start-up device of various water quality sensors to ensure that on-line monitoring and assessment of water sudden pollution accidents is timely and effective.

Figure 16:
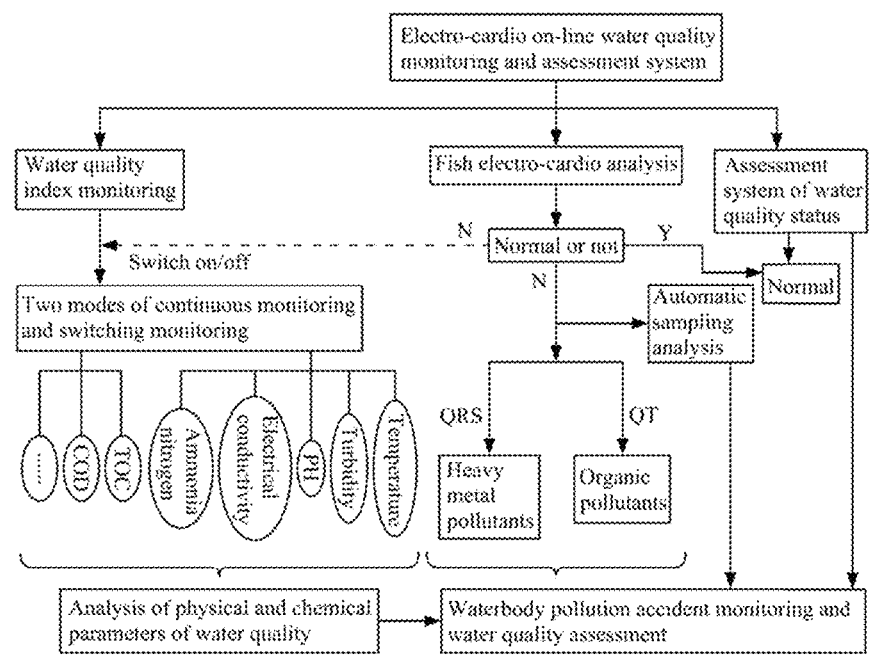
FIG. 16 is a schematic diagram of an on-line monitoring system for water sudden pollution based on fish electro-cardio according to one or more embodiments of the present disclosure.

An aspect of the present disclosure provides a method for online monitoring water sudden pollution based on fish electro-cardio, as shown in FIG. 16. The method is based on the real-time and miniaturized fish electro-cardio acquisition system, and the method includes the following steps.

The fish electro-cardio signals acquired by the real-time and miniaturized fish electro-cardio acquisition system before the fish is exposed to the water to be tested and at several specific time points after the fish is exposed to the water to be tested are obtained.

An electro-cardio index of the acquired electro-cardio signals of respective fishes in a QRS interval and a QT interval are respectively extracted.

A change of the electro-cardio index is analyzed before the fish is exposed to the water to be tested and at the several specific time points after the fish is exposed to the water to be tested; if the change exceeds a preset threshold, a type of the pollutants is determined and water quality parameters acquired by a sensor are recorded, and otherwise, the water to be tested meets the standard.

The type of the pollutant and the amount and range of the pollution are further determined according to the water quality parameters acquired by the sensor.

Further, in the method, the electro-cardio signals are respectively acquired from several fishes before the fishes are exposed to the water to be tested and at several specific time points after the fishes are exposed to the water to be tested.

Further, in the method, the fish body electro-cardio signals are pre-processed, and the pre-processing includes filtering and interference removal.

Further, the water quality parameters include temperature, turbidity, pH, electrical conductivity, ammonia nitrogen, total phosphorus, total nitrogen, TOC, COD, and water chlorophyll, and contents of Cd, Cr, Cu, Fe, Zn, Pb, and Mn, etc.

Further, in the method, the fish electro-cardio signals before the fish is exposed to the water to be tested and at the several specific time points after the fish is exposed to the water to be tested and the water quality parameters acquired by the sensor are simultaneously obtained for on-line monitoring of the water sudden pollution.

Further, in the method, the sensors of conventional five parameters (temperature, turbidity, pH, electrical conductivity, ammonia nitrogen) are normally operated, and the electro-cardio abnormality is the start switch of other water quality monitoring instruments (that is, except for the sensors of the five parameters, the instruments with other parameters are power-on but not activated. Only ECG abnormality leads to the startup of monitoring and analysis).

An aspect of the present disclosure also provides a computer-readable storage medium, in which a plurality of instructions are stored, and these instructions are suitable to be loaded by a processor of the terminal device and to perform the method for assessing water heavy metal pollution using a fish QRS interval, and the method for assessing water organic pollution using a fish QT interval and/or the method for online monitoring water sudden pollution based on fish electro-cardio.

An aspect of the present disclosure further provides a terminal device, that is further an internet terminal device, which includes a processor for implementing each instruction and a computer-readable storage medium for storing a plurality of instructions suitable to be loaded by a processor and to perform the method for assessing water heavy metal pollution using a fish QRS interval, and the method for assessing water organic pollution using a fish QT interval and/or the method for online monitoring water sudden pollution based on fish electro-cardio.

These computer-executable instructions run in the device so that the device performs the methods or processes described in each embodiment of the present disclosure.

In the present embodiment, a computer program product may include a computer-readable storage medium which is loaded with computer-readable program instructions for performing each aspect of the present disclosure. The computer-readable storage medium can be a tangible device that can hold and store the instructions for use by an instruction execution device. The computer-readable storage medium can be, for example, but not limited to, electrical storage device, magnetic storage device, optical storage device, electromagnetic storage device, semiconductor storage device, or any suitable combination of the foregoing. More specific examples (non-exhaustive list) of computer-readable storage media include portable computer disks, hard disks, random access memory (RAM), read-only memory (ROM), erasable programmable read-only memory (EPROM or flash memory), static random access memory (SRAM), portable compact disk read-only memory (CD-ROM), digital versatile disk (DVD), memory stick, floppy disk, mechanical encoding device, punched card or convex structure in groove such as on which instructions are stored, and any suitable combination of the foregoing. The computer-readable storage medium as used herein is not interpreted as transient signal itself, such as radio wave or other freely propagating electromagnetic waves, an electromagnetic wave propagating through wave guide or other transmission medium (eg, light pulse passing through fiber optic cable), or electrical signals transmitted through wires.

The computer-readable program instructions described herein can be downloaded to each computing/processing device from the computer-readable storage medium, or downloaded to an external computer or an external storage device via network, such as Internet, local area network, wide area network, and/or wireless network. The network may include copper transmission cables, fiber optic transmissions, wireless transmissions, routers, firewalls, switches, gateway computers, and/or edge servers. A network adapter card or network interface in each computing/processing device receives computer-readable program instructions from the network and forwards the computer-readable program instructions for its storage in the computer-readable storage medium in each computing/processing device.

Computer program instructions for performing the operations of the present disclosure may be assembly instructions, instruction set architecture (ISA) instructions, machine instructions, machine related instructions, microcode, firmware instructions, state setting data, or source code or object code written in any combination in one or more programming languages which include object-oriented programming languages such as C++, and conventional procedural programming languages such as a "C" language or similar programming language. The computer-readable program instructions can execute entirely on the user's computer, execute partly on the user's computer, execute as a stand-alone software package, execute partly on the user's computer and partly on the remote computer, or execute entirely on the remote computer or server. In the case of remote computer, the remote computer can be connected to the user's computer through any kind of network, including local area network (LAN) or wide area network (WAN), or can be connected to an external computer (eg, be connected through Internet provided by Internet service provider). In some embodiments, the electronic circuit, such as a programmable logic circuit, a field programmable gate array (FPGA), or a programmable logic array (PLA), can be personally customized by utilizing state information of computer-readable program instructions. The customized electronic circuit can perform computer-readable program instructions, thereby implementing various aspects of the present disclosure.

An aspect of the present disclosure provides an on-line monitoring system for water sudden pollution based on fish electro-cardio.

The system continuously acquires electro-cardio on-line in real-time while keeping fish swimming in the normal state, and monitors on-line various water quality indexes, which include temperature, turbidity, pH, electrical conductivity, ammonia nitrogen, total phosphorus, total nitrogen, TOC, COD, chlorophyll and sensors for various heavy metal (Cd, Cr, Cu, Fe, Zn, Pb, Mn, etc.) and the system is equipped with real-time on-line water quality sampling technology. The various water quality parameters are determined by a monitoring and analysis platform. If the electro-cardio parameters are abnormal during the water quality monitoring process, then the electro-cardio parameters abnormality is the start switch of the real-time on-line water quality sampling technology and the operation of parameters other than the conventional five parameters. Therefore, the technology combines the analysis and monitoring based on fish electro-cardio parameters and the analysis and assessment of water quality parameters, and can timely and promptly assess the water sudden pollution accidents, thereby reducing the hazards.

As shown in FIG. 17, the on-line monitoring system for water sudden pollution based on fish electro-cardio is implemented based on the method for online monitoring water sudden pollution based on fish electro-cardio, and the system includes a real-time and miniaturized fish electro-cardio acquisition device, a signal receiving device, a water quality sensor, and a computor terminal.

The real-time and miniaturized fish electro-cardio acquisition device is provided on a fish through a carrier matching with a profile of the fish, and the carrier is configured to ensure that the carrier and the real-time and miniaturized fish electro-cardio acquisition device as a whole are equal in gravity and buoyancy.

The real-time and miniaturized fish electro-cardio acquisition device includes a waterproof housing, where a miniature electro-cardio signal processing device, a storage device connected to the miniature electro-cardio signal processing device, and a battery are fixedly arranged in the waterproof housing. The miniature electro-cardio signal processing device is connected to the electrode through wires; an outlet for leading the electrode is provided at a bottom of the waterproof housing; the electrode is inserted into the pericardial cavity of a fish to acquire the original electro-cardio signals which are then transmitted to the miniature electro-cardio signal processing device for processing; a side of the waterproof housing is provided with a through hole for placing the signal transmitting device; a transmitting end of the signal transmitting device passes through the through hole from an inside of the body of the waterproof housing and is sealedly connected to the through hole. The infrared signal transmitting device is connected to the battery and the miniature electro-cardio signal processing device, respectively, and transmits the processed electro-cardio signals to the signal receiving device matched with the signal transmitting device to complete the real-time electro-cardio signal acquisition of the fish.

The infrared signal receiving device is provided on the side wall of the water tank for receiving the processed electro-cardio signals and transmitting the received electro-cardio signals to the computor terminal.

The water quality sensor receives the acquired signals of the computor terminal to acquire and send water quality parameters to the computor terminal, where the water quality parameters include temperature, turbidity, pH, electrical conductivity, ammonia nitrogen, total phosphorus, total nitrogen, TOC, COD, chlorophyll, Cd, Cr, Cu, Fe, Zn, Pb, and Mn.

The water quality sensor includes a temperature sensor, a turbidity sensor, a pH sensor, an electrical conductivity sensor, an ammonia nitrogen sensor, a total phosphorus sensor, a total nitrogen sensor, a TOC sensor, a COD sensor, a chlorophyll sensor, and a heavy metal sensors; where the heavy metal sensor includes a cadmium sensor, a chrome sensor, a copper sensor, an iron sensor, a zinc sensor, a lead sensor, and a manganese sensor.

The electrode of the system includes an acquisition electrode and a reference electrode; where the acquisition electrode is embedded in the pericardial cavity of the fish which is used for electro-cardio signal acquisition, and the reference electrode is embedded near the cloacal orifice of the fish which is used for electro-cardio signal acquisition, and the acquisition electrode and the reference electrode embedded share the same length in the fish. The electro-cardio signal acquisition memory can acquire the electro-cardio signals of the fish, filter the interference signals through the filtering technology, and store the filtered signals, which has the functions of acquisition, filtering and signal storage. The acquired electro-cardio signals, may be emitted by signal transmitting device, and be transmitted through the water and air, then be received by the signal receiving device. The wire connects to the electro-cardio signal acquisition memory, and is mainly used for transmitting signals, and departs from one end of the waterproof housing. There are three wires manufactured by coating a sheath on copper wire, where the sheath is made of a thermoplastic elastomer (TPE) rubber. One end of respective wires is connected to one electrode, and are made of silver fine needle with a diameter of 0.25 mm and needle tip for piercing into the pericardial cavity of the fish. A metal corresponding interface in contact with the battery is provided at the other end of the electro-cardio acquisition memory, so as to connect with the battery, and energize the acquisition device. The waterproof housing, made of metal alloy, encapsulates the electro-cardio acquisition memory and the battery in threaded connection, facilitating the disassembly and replacement of the battery. The saddle-shaped carrier is made of the low-density material and is printed by 3D. After the carrier fits with the device, the combination can be placed in the water without sinking or floating, achieving the equal state of the gravity and the buoyancy, avoiding the load on the fish and ensuring that the fish swims in a normal state.

Where, in order to ensure on-line monitoring and analysis of water sudden pollution accidents, the water quality on-line monitoring and assessment system are divided into two operating modes: the first mode is that the instruments in the system are activated to monitor the water quality, and various water quality indexes are monitored on-line in real-time to ensure comprehensive and specific monitoring of water quality. However, this mode relatively consumes more electrical energy, etc. The second mode is that the sensors only for the conventional five parameters, namely temperature, turbidity, pH, electrical conductivity, and ammonia nitrogen, are activated to monitor the water quality, if the electro-cardio index is abnormal, other water quality monitoring instruments will be activated for comprehensive monitoring and analysis.

Under the stress of different heavy metal pollutants, the electro-cardio of zebrafish will change differently. QRS interval and heavy metal pollutant stress have significant correlation, and heavy metal pollutants in water quality can be monitored by studying and analyzing the QRS interval. QT interval and organic pollutant stress have significant correlation, and organic pollutants in water quality can be monitored by studying and analyzing QT interval. Therefore, whether the type of pollutant is organic or heavy metal can be determined by combining abnormality of electro-cardio parameters. Furthermore, the specific monitoring results of the water quality parameter heavy metal sensors and the on-line analysis results of TOC and COD are combined to further determine the specific pollutant types and the amount and range of the pollution, thereby timely, efficiently and correctly realizing on-line monitoring and assessment for water pollution accidents. Where real-time on-line water quality sampling technology is equipped, and the electro-cardio abnormality is the start switch of automatic sampling of water quality. In this way, once the electro-cardio parameters abnormality is found through the monitoring and analysis platform, the water quality will be sampled on-line in real-time.

Advantages of the disclosure are as follows.

1. The real-time and miniaturized fish electro-cardio acquisition device of the present disclosure is small and light, and is convenient for the fish to be carried on the fish; the carrier can bear the miniature electro-cardio signal processing device and the battery which both encapsulated by the waterproof housing, and the buoyancy of the carrier is equal to the gravity of the device, so that there is no external force and load to the fish, enabling that fish swims spontaneously in a normal state in the water.

2. The waterproof housing, provided in the real-time and miniaturized fish electro-cardio acquisition device of the present disclosure, envelops the miniature electro-cardio signal processing device, the storage device connected to the processing device, the infrared signal transmitting device and the battery, so that the entire device can retain in water and acquire electro-cardio signals therein.

3. The infrared signal transmitting device, provided in the real-time and miniaturized fish electro-cardio acquisition device of the present disclosure, can be used as a signal transmitter to emit electro-cardio signals, so that the signals can be transmitted through the aqueous phase to the gas phase, and be received by the signal receiving device.

4. The real-time and miniaturized fish electro-cardio acquisition device of the present disclosure is capable of continuously acquiring fish electro-cardio signals in real-time, and capable of filtering and denoising the acquired electro-cardio signals, and capable of storing the acquired electro-cardio signals.

5. The real-time and miniaturized fish electro-cardio acquisition device of the present disclosure, can retain in water and acquire the electro-cardio signals therein, thus the technology can continuously acquire fish electro-cardio in water for a long time with enough battery power.

6. The water quality assessment method and device based on fish electro-cardio index of the present disclosure, provide an effective solution for assessing water quality by utilizing electro-cardio indexes as indexes, realizing easy and executable fish electro-cardio indexes acquisition and the assessment of the organic pollutants in water quality by utilizing fish electro-cardio indexes as indexes; various organic pollutants in water quality are assessed by various fish electro-cardio indexes, and QT interval is filtered out from fish electro-cardio indexes for monitoring organic pollutants in water quality.

7. The method, device and system for assessing water heavy metal pollution by fish QRS interval of the present disclosure, provide an effective solution for assessing water heavy metal pollution by utilizing electro-cardio indexes as indexes, realizing easy and executable fish electro-cardio indexes acquisition and the assessment of the heavy metals in water quality by utilizing fish electro-cardio indexes as indexes; specifically, the heavy metals in water quality are assessed by the electro-cardio index of the fish QRS interval.

8. The method, device and system for online monitoring water sudden pollution based on fish electro-cardio of the present disclosure, combines on-line monitoring for water sudden pollution accidents based on fish electro-cardio index and the technology of analysis and assessment of water quality parameters, and electro-cardio abnormality is the start switch of other water quality monitoring instruments, and the monitoring and analysis are only performed when the electro-cardio parameters are abnormal, thereby effectively saving electrical energy. The electro-cardio parameters abnormality is found through the monitoring and analysis platform, then the water quality will be sampled on-line in real-time. Furthermore, the specific monitoring results of the water quality parameter heavy metal sensor and the on-line analysis results of TOC and COD are combined to further determine the specific pollutant types and the amount and range of the pollution, thereby timely, efficiently and correctly realizing on-line monitoring and assessment of water pollution accidents, and ensuring timely monitoring and assessment feedback of water sudden pollution accidents, and combining biological monitoring with physical and chemical monitoring.

The above description is only the exemplary embodiments of the present application, and is not intended to limit the present application, and various modifications and changes may be made by those skilled in the art. Any modifications, equivalent substitutions, improvements, etc. made within the spirit and principles of this application shall fall within the scope of the present application. Therefore, the present disclosure is not limited to the embodiments shown herein, but accords with the broadest scope according to the principles and novel features disclosed herein.

What is claimed is:

1. A real-time and miniaturized fish electro-cardio acquisition device, comprising
    a waterproof housing comprising a body and a waterproof cover sealedly connected to the body;
    wherein a miniature electro-cardio signal processing device, a storage device connected to the miniature electro-cardio signal processing device and a battery are fixedly arranged in the body; the miniature electro-cardio signal processing device is connected to an electrode through wires; a bottom of the waterproof housing is provided with an outlet for leading the electrode, wherein the electrode is inserted into a pericardial cavity of a fish to acquire original electro-cardio signals which are then transmitted to the miniature electro-cardio signal processing device for processing;
    a side of the waterproof housing is provided with a through hole for placing an infrared signal transmitting device; a transmitting end of the infrared signal transmitting device passes through the through hole from an inside of the body of the waterproof housing and is sealedly connected to the through hole; the infrared signal transmitting device respectively connects to the battery and the miniature electro-cardio signal processing device, and transmits the processed electro-cardio signals to an infrared signal receiving device matched with the infrared signal transmitting device to complete the real-time electro-cardio signal acquisition of the fish; the miniature electro-cardio signal processing device comprises an electro-cardio acquisition circuit, an electro-cardio bandpass amplifying circuit and a low-power consumption processor connected in sequence; the electro-cardio acquisition circuit is configured to convert the original electro-cardio signals acquired by the electrode into electro-cardio analog signals for output; the electro-cardio bandpass amplifying circuit is configured to process the electro-cardio analog signals by bandpass filtering and signal amplification; the low-power consumption processor is configured to process the filtered and amplified electro-cardio signals by wavelet decomposition and reconstruct a filtered signal coefficient using a wavelet decomposition structure to obtain denoised electro-cardio signals; the miniature electro-cardio signal processing device, the storage device and the battery are all provided on a circuit board; and two slots are symmetrically provided in the body for positioning the circuit board and the circuit board has a width equal to a spacing between the two slots; the real-time and miniaturized fish electro-cardio acquisition device further comprises a power management circuit; the battery is connected to the power management circuit and is respectively connected to the miniature electro-cardio signal processing device and the storage device through the power management circuit; and the power management circuit is provided on the circuit board.

2. A real-time and miniaturized fish electro-cardio acquisition system, comprising:
the real-time and miniaturized fish electro-cardio acquisition device of claim 1 that is worn by a fish; and
an infrared signal receiving device arranged on a water tank;
wherein the infrared signal receiving device is used in conjunction with an infrared signal transmitting device provided in the real-time and miniaturized fish electro-cardio acquisition device;
the real-time and miniaturized fish electro-cardio acquisition device is arranged on the fish through a carrier matching with a profile of the fish; and the carrier is configured to ensure that the carrier and the real-time and miniaturized fish electro-cardio acquisition device as a whole are equal in gravity and buoyancy;
the real-time and miniaturized fish electro-cardio acquisition system comprises a waterproof housing, wherein a miniature electro-cardio signal processing device, a storage device connected to the miniature electro-cardio signal processing device and a battery are fixedly arranged in the waterproof housing; the miniature electro-cardio signal processing device is connected to an electrode through wires; an outlet for leading the electrode is provided at a bottom of the waterproof housing; the electrode is inserted into a pericardial cavity of a fish to acquire original electro-cardio signals which are then transmitted to the miniature electro-cardio signal processing device for processing; a through hole for placing an infrared signal transmitting device is provided on a side of the waterproof housing, and a transmitting end of the infrared signal transmitting device passes through the through hole from an inside of a body of the waterproof housing and is sealedly connected to the through hole; the infrared signal transmitting device is connected to the battery and the miniature electro-cardio signal processing device, respectively and transmits the processed electro-cardio signals to an infrared signal receiving device matched with the infrared signal transmitting device to complete the real-time electro-cardio signal acquisition of the fish; and
the infrared signal receiving device is provided on a side wall of the water tank for receiving the processed electro-cardio signals.

3. The system of claim 2, wherein the carrier is made of a low-density material to ensure that the carrier and the real-time and miniaturized fish electro-cardio acquisition device as a whole are equal in gravity and buoyancy; the waterproof housing comprises the body and a waterproof cover sealedly connected to the body; and
a plurality of infrared signal receiving devices are provided and evenly distributed on a plurality of side walls of the water tank.

4. A method of monitoring water environment based on the system of claim 2, comprising: receiving real-time fish electro-cardio signals acquired by the real-time and miniaturized fish electro-cardio acquisition system in a certain period of time to monitor the water environment.

5. A water environment monitoring system, comprising:
the system of claim 2 and a computer;
wherein the computer is configured to receive real-time fish electro-cardio signals acquired by the real-time and miniaturized fish electro-cardio acquisition system in a certain period of time to monitor the water environment.

6. A method for determining a fish electro-cardio index in the assessment of water organic pollution based on the system of claim 2, comprising:
gathering fish electro-cardio signals acquired by the real-time and miniaturized fish electro-cardio acquisition system respectively before and after the fish is exposed to a solution containing a specific organic compound and respectively extracting various electro-cardio indexes;
analyzing the correlation between environmental stress and respective extracted electro-cardio indexes according to Pearson Correlation Analysis to select an electro-cardio index suitable for the assessment of water quality with respect to this specific organic compound; and
analyzing and assessing a linear regression model between the environmental stress and respective electro-cardio indexes according to Akaike Information Criterion and the residual sum of squares to finally obtain an electro-cardio index suitable for the assessment of water quality with respect to the specific organic compound.

7. The method of claim 6, wherein electro-cardio signals are acquired at different time points from multiple fishes respectively exposed to different concentrations of the specific organic compound; and
the extracted electro-cardio indexes comprise: P-wave amplitude, Q-wave amplitude, R-wave amplitude, S-wave amplitude, T-wave amplitude and P-R interval, QRS interval, S-T interval and Q-T interval.

8. The method of claim 6, further comprising: pre-processing the fish electro-cardio signals, wherein the pre-processing comprises filtering and interference removal;
the method further comprises: determining a trend of the effects of the specific organic compound concentration and time on the fish electro-cardio indexes before analyzing the correlation between the environmental stress and respective extracted electro-cardio indexes according to the Pearson Correlation Analysis; and
a significant correlation is determined through this method between the QT interval in the fish electro-cardio indexes and the organic compound stress in water so that the QT interval is suitable for assessing water quality with respect to this specific organic compound.

9. A system for implementing the method of claim 6, comprising:
a real-time and miniaturized fish electro-cardio acquisition system and a computor terminal.

10. A method for assessing water organic pollution using a fish QT interval based on the method of claim 6, comprising:

receiving fish electro-cardio signals acquired by a real-time and miniaturized fish electro-cardio acquisition system respectively before and after the fish is exposed to water to be tested;

extracting an electro-cardio index of fish electro-cardio signals in the QT interval; and comparing the electro-cardio index extracted from the fish electro-cardio signals respectively acquired before and after the fish is exposed to the water to be tested to obtain the change of the electro-cardio index, thereby determining an organic pollutant in the water to be tested.

11. A system for implementing the method of claim 10, comprising:

a real-time and miniaturized fish electro-cardio acquisition system and a computor terminal.

12. A computer-readable storage medium, wherein a plurality of instructions are stored in the computer-readable storage medium; wherein the instructions are loaded by a processor of a terminal device to perform the method of claim 10.

13. A terminal device, wherein the terminal device is an internet terminal device, and comprises a computer-readable storage medium for storing a plurality of instructions and a processor for executing the instructions; wherein the instructions are suitable to be loaded by the processor to perform the method of claim 10.

14. A method for assessing heavy metal pollution in water based on fish QRS interval using the system of claim 2, comprising:

obtaining fish electro-cardio signals acquired by the real-time and miniaturized fish electro-cardio acquisition system before the fish is exposed to water to be tested and at several specific time points after the fish is exposed to the water to be tested;

extracting an electro-cardio index of acquired electro-cardio signals of respective fishes in the QRS interval; and analyzing a change of the electro-cardio index before the fish is exposed to the water to be tested and at several specific time points after the fish is exposed to the water to be tested; if the change exceeds a preset threshold, the heavy metal content of the water to be tested exceeds the standard, and otherwise, the heavy metal content of the water to be tested meets the standard.

15. The method of claim 14, wherein fish electro-cardio signals of multiple fishes are acquired respectively before the fishes are exposed to the water to be tested and at several specific time points after the fishes are exposed to the water to be tested; and the method further comprises: pre-processing the fish electro-cardio signals, wherein the pre-processing comprises filtering and interference removal.

16. A system for implementing the method of claim 14, comprising:

a real-time and miniaturized fish electro-cardio acquisition system;

an infrared signal receiving device; and a computor terminal;

wherein the real-time and miniaturized fish electro-cardio acquisition system is provided on a fish through a carrier matching with a profile of the fish; and the carrier is configured to ensure that the carrier and the real-time and miniaturized fish electro-cardio acquisition system as a whole are equal in gravity and buoyancy;

the real-time and miniaturized fish electro-cardio acquisition system comprises a waterproof housing in which a miniature electro-cardio signal processing device, a storage device connected to the processing device and a battery are fixedly arranged; the miniature electro-cardio signal processing device is connected to an electrode through wires; a bottom of the waterproof housing is provided with an outlet for leading the electrode; the electrode is inserted into a pericardial cavity of the fish to acquire original electro-cardio signals which are transmitted through wires to the miniature electro-cardio signal processing device for processing; a through hole for placing an infrared signal transmitting device is provided on a side of the waterproof housing; a transmitting end of the infrared signal transmitting device passes through the through hole from an inside of a body of the waterproof housing and is sealedly connected to the through hole; the infrared signal transmitting device is connected to the battery and the miniature electro-cardio signal processing device, respectively, and transmits the processed electro-cardio signals to the infrared signal receiving device matched with the infrared signal transmitting device to complete the real-time fish electro-cardio signal acquisition; and the infrared signal receiving device is arranged on a side wall of a water tank for receiving the processed electro-cardio signals and transmitting the received electro-cardio signals to the computor terminal.

17. The system of claim 16, wherein the electrode of the system comprises an acquisition electrode and a reference electrode, wherein the acquisition electrode is embedded in the pericardial cavity of a fish which is used for electro-cardio signal acquisition, and the reference electrode is embedded near a cloacal orifice of the fish which is used for electro-cardio signal acquisition; and the acquisition electrode and the reference electrode embedded share the same length in the fish.

18. A method for online monitoring water sudden pollution based on fish electro-cardio using the system of claim 2, comprising:

obtaining fish electro-cardio signals acquired by the real-time and miniaturized fish electro-cardio acquisition system respectively before and at several specific time points after a fish is exposed to water to be tested;

respectively extracting an electro-cardio index of the acquired electro-cardio signals of respective fishes in a QRS interval and a QT interval;

analyzing a change of the electro-cardio index before the fish is exposed to the water to be tested and at the several specific time points after the fish is exposed to the water to be tested; if the change exceeds a preset threshold, a type of a pollutant is determined and water quality parameters acquired by a sensor are recorded, and otherwise, the water to be tested meets the standard; and determining the type of the pollutant and the amount and range of the pollution according to the water quality parameters acquired by the sensor.

19. The method of claim 18, wherein electro-cardio signals are respectively acquired from several fishes before the fishes are exposed to the water to be tested and at several specific time points after the fishes are exposed to the water to be tested.

20. The method of claim 18, further comprising: preprocessing the fish electro-cardio signals; wherein the preprocessing comprises filtering and interference removal.

21. The method of claim 18, wherein the water quality parameters comprise temperature, turbidity, pH, electrical conductivity, ammonia nitrogen, total phosphorus, total nitrogen, TOC, COD, chlorophyll, Cd, Cr, Cu, Fe, Zn, Pb and Mn.

22. The method of claim 18, wherein the fish electro-cardio signals before the fish is exposed to the water to be tested and at the several specific time points after the fish is exposed to the water to be tested and the water quality parameters acquired by the sensor are simultaneously obtained for on-line monitoring of the water sudden pollution.

23. A system for implementing the method of claim 18, comprising:
 a real-time and miniaturized fish electro-cardio acquisition device, a signal receiving device, a water quality sensor, and a computor terminal;
 wherein the real-time and miniaturized fish electro-cardio acquisition device is provided on a fish through a carrier matching with a profile of the fish, and the carrier is configured to ensure that the carrier and the real-time and miniaturized fish electro-cardio acquisition device as a whole are equal in gravity and buoyancy;
 the real-time and miniaturized fish electro-cardio acquisition device comprises a waterproof housing, where a miniature electro-cardio signal processing device, a storage device connected to the miniature electro-cardio signal processing device, and a battery are fixedly arranged in the waterproof housing; the miniature electro-cardio signal processing device is connected to an electrode through wires; an outlet for leading the electrode is provided at a bottom of the waterproof housing; the electrode is inserted into a pericardial cavity of the fish to acquire original electro-cardio signals which are then transmitted to the miniature electro-cardio signal processing device for processing; a through hole for placing an infrared signal transmitting device is provided on a side of the waterproof housing, and a transmitting end of the infrared signal transmitting device passes through the through hole from an inside of a housing body of the waterproof housing and is sealedly connected to the through hole; the infrared signal transmitting device is connected to the battery and the miniature electro-cardio signal processing device, respectively, and transmits the processed electro-cardio signals to an infrared signal receiving device matched with the infrared signal transmitting device to complete the real-time electro-cardio signal acquisition of the fish;
 the infrared signal receiving device is provided on a side wall of a water tank for receiving the processed electro-cardio signals and transmitting the received electro-cardio signals to the computor terminal;
 the water quality sensor receives acquired signals of the computor terminal to acquire and send water quality parameters to the computor terminal, wherein the water quality parameters comprise temperature, turbidity, pH, electrical conductivity, ammonia nitrogen, total phosphorus, total nitrogen, TOC, COD, chlorophyll, Cd, Cr, Cu, Fe, Zn, Pb and Mn.

24. The system of claim 23, wherein the water quality sensor comprises a temperature sensor, a turbidity sensor, a pH sensor, an electrical conductivity sensor, an ammonia nitrogen sensor, a total phosphorus sensor, a total nitrogen sensor, a TOC sensor, a COD sensor, a chlorophyll sensor, and a heavy metal sensor; wherein the heavy metal sensor comprises a cadmium sensor, a chrome sensor, a copper sensor, an iron sensor, a zinc sensor, a lead sensor, and a manganese sensor; and
 the electrode of the system comprises an acquisition electrode and a reference electrode; wherein the acquisition electrode is embedded in the pericardial cavity of the fish which is used for electro-cardio signal acquisition, and the reference electrode is embedded near a cloacal orifice of the fish which is used for the electro-cardio signal acquisition; and the acquisition electrode and the reference electrode share the same length in the fish.

* * * * *